US010274460B2

(12) United States Patent
Walton et al.

(10) Patent No.: US 10,274,460 B2
(45) Date of Patent: Apr. 30, 2019

(54) CAPILLARY ARRAY CARTRIDGE FOR CAPILLARY ELECTROPHORESIS SYSTEMS

(71) Applicant: LIFE TECHNOLOGIES CORPORATION, Carlsbad, CA (US)

(72) Inventors: Ian Walton, Redwood City, CA (US); Achim Karger, Foster City, CA (US); Alexander Khorlin, Mountain View, CA (US); Michael Simon, San Francisco, CA (US); Adam Sannicandro, San Francisco, CA (US); Alexander Dukhovny, San Francisco, CA (US); Robert Cobene, Santa Clara, CA (US); Dan Kline, Vista, CA (US); John Dixon, Moss Beach, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 26 days.

(21) Appl. No.: 15/124,168

(22) PCT Filed: Mar. 6, 2015

(86) PCT No.: PCT/US2015/019307
§ 371 (c)(1),
(2) Date: Sep. 7, 2016

(87) PCT Pub. No.: WO2015/134943
PCT Pub. Date: Sep. 11, 2015

(65) Prior Publication Data
US 2017/0176385 A1    Jun. 22, 2017

Related U.S. Application Data

(60) Provisional application No. 61/949,961, filed on Mar. 7, 2014.

(51) Int. Cl.
*G01N 27/447* (2006.01)

(52) U.S. Cl.
CPC . *G01N 27/44791* (2013.01); *G01N 27/44743* (2013.01); *G01N 27/44756* (2013.01); *G01N 27/44704* (2013.01)

(58) Field of Classification Search
CPC .................... G01N 27/447–27/44795; B01D 57/00–57/02; C02F 1/4696; B81B 1/00–1/008
(Continued)

(56) References Cited

U.S. PATENT DOCUMENTS 5,993,634 A    11/1999 Simpson et al.
6,156,178 A    12/2000 Mansfield et al.
(Continued)

FOREIGN PATENT DOCUMENTS

CN    1146017 A    3/1997
CN    101013083 A    8/2007
(Continued)

OTHER PUBLICATIONS

International Search Report and Written Opinion for PCT/US2015/019307, dated Jun. 10, 2015.
(Continued)

*Primary Examiner* — Bach T Dinh
(74) *Attorney, Agent, or Firm* — Jones Robb, PLLC

(57) ABSTRACT

The present disclosure relates, in some embodiments, to an apparatus for conducting a capillary electrophoresis assay. The apparatus can comprise a capillary array comprising an anode end and a cathode end, the capillary array provided in a housing further comprising a reservoir configured to house a separation medium and an anode buffer. The system can also comprise an injection mechanism configured to deliver sample to the cathode end of the capillary array, and a temperature control zone, wherein the temperature control
(Continued)

zone is configured to control the temperature of the interior of the housing.

16 Claims, 23 Drawing Sheets

(58) Field of Classification Search
USPC ................ 204/450–470, 546–550, 600–621, 204/643–645
See application file for complete search history.

(56) References Cited

U.S. PATENT DOCUMENTS

| | | | |
|---|---|---|---|
| 6,364,516 B1* | 4/2002 | Li | G01N 27/44721 204/451 |
| 6,635,164 B1 | 10/2003 | Takashi et al. | |
| 2001/0040096 A1 | 11/2001 | Yamamoto et al. | |
| 2002/0123073 A1* | 9/2002 | Amirkhanian | G01N 27/44721 435/7.1 |
| 2003/0155245 A1* | 8/2003 | Morioka | G01N 27/44721 204/601 |
| 2005/0000812 A1 | 1/2005 | Couderc et al. | |
| 2006/0176481 A1 | 8/2006 | Forest et al. | |
| 2007/0065344 A1 | 3/2007 | Carson et al. | |
| 2011/0290648 A1* | 12/2011 | Majlof | G01N 27/44708 204/452 |
| 2013/0115607 A1* | 5/2013 | Nielsen | C12Q 1/68 435/6.12 |
| 2015/0241389 A1* | 8/2015 | Hill | G01N 27/44704 204/603 |

FOREIGN PATENT DOCUMENTS

| | | |
|---|---|---|
| CN | 101105455 A | 1/2008 |
| CN | 102023146 A | 4/2011 |
| EP | 1467202 A2 | 10/2004 |
| WO | 9429712 A1 | 12/1994 |
| WO | 2010141921 A1 | 12/2010 |
| WO | 2013059750 A1 | 4/2013 |

OTHER PUBLICATIONS

Casado-Terrones, et al. "Simple luminescence detectors using a light-emitting diode or a Xe lamp, optical fiber and charge-coupled device, or photomultiplier for determining proteins in capillary electrophoresis: A critical comparison", Analytical Biochemistry, Academic Press Inc, New York, vol. 365, No. 1, Apr. 25, 2007 (Apr. 25, 2007), pp. 82-90.

* cited by examiner

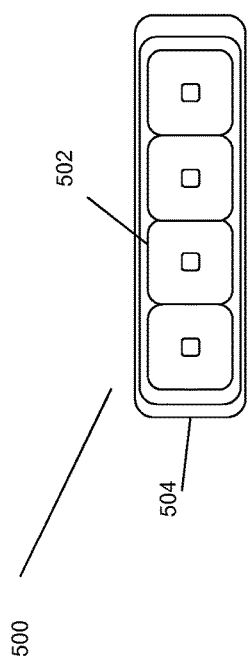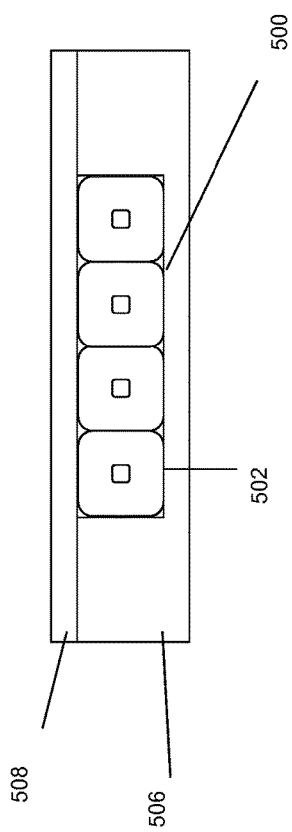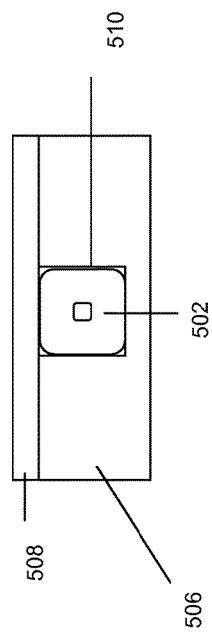
Figure 5

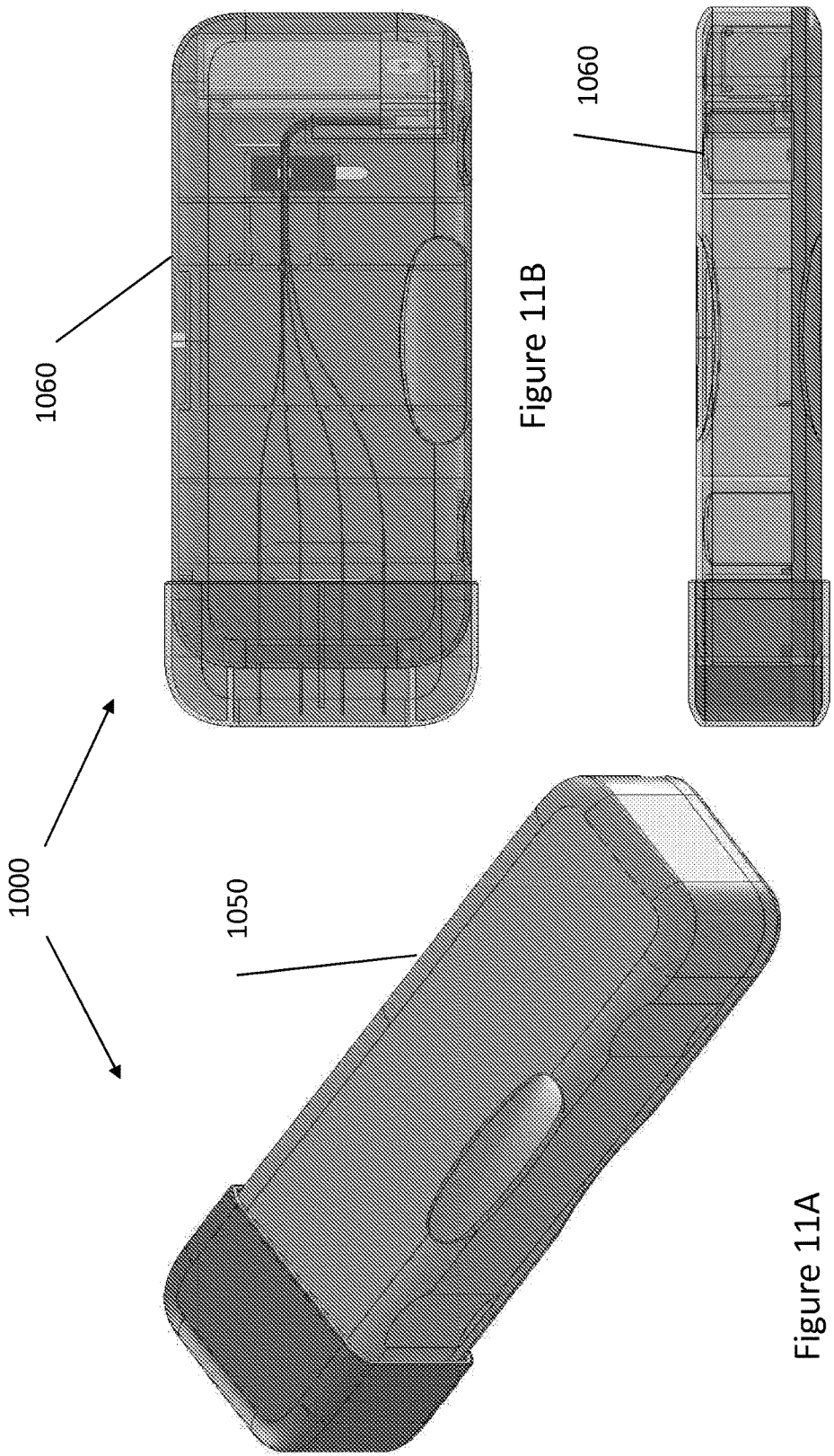

CAPILLARY ARRAY CARTRIDGE FOR CAPILLARY ELECTROPHORESIS SYSTEMS

FIELD OF THE DISCLOSURE

The present disclosure relates to a multi-capillary electrophoresis apparatus and components thereof. The present disclosure further relates to structures and mechanisms designed to house multiple components of a multi-capillary electrophoresis apparatus.

BACKGROUND

Capillary electrophoresis devices generally provide certain major components that include, for example, a capillary array, a separation medium source for providing medium to the capillaries (e.g., a polymer), a sample injection mechanism, an optical detector component, an electrode, and anode buffer source on one end of the capillaries, and a cathode buffer source on the other end of the capillaries. Capillary electrophoresis devices generally also provide various heating components and zones to regulate the temperature of many of the aforementioned components. Regulating the temperature of many of these components can improve quality of results.

To provide the major components of a capillary electrophoresis device while regulating the temperature of many of these components, current capillary electrophoresis devices use multiple structures to house these components and connect or couple these structures together to provide a working capillary electrophoresis device. Using multiple structures has disadvantages. For example, each of the interconnected structures may require its own temperature regulating mechanisms, thus creating independent temperature control zones. Each of these zones would then require associated individual control mechanisms. This multi-structure design increases the overall number of components in the apparatus, complicates the temperature control scheme, and increases the chances of component failure due to the sheer number of components involved. FIG. 1 shows one such design, illustrating multiple temperature control zones TCM0 to TCM5.

The use of multiple interconnected structures is also not user-friendly. For example, attaching the separation medium (hereinafter referred to as "polymer") source to the capillary array can be complicated and runs the risk of introducing bubbles or other artifacts each time the array is detached and attached to the polymer source. Moreover, the user, rather than the manufacturer, generally must attach the buffer source to the array, and must do it multiple times through the life of the capillary array.

It is therefore desirable to provide a capillary electrophoresis apparatus with a reduced number of interconnected structures to reduce the number of necessary heating zones, reduce user handling of the structures, reduce likelihood of component failure, and reduce introduction of bubbles and other artifacts into the apparatus.

SUMMARY OF THE DISCLOSURE

The present disclosure relates, in some embodiments, to an apparatus for conducting a capillary electrophoresis assay. The apparatus can comprise a capillary array comprising an anode end and a cathode end, the capillary array provided in a housing further comprising a reservoir configured to house a separation medium and an anode buffer. The system can also comprise an injection mechanism configured to deliver sample to the cathode end of the capillary array, and a temperature control zone, wherein the temperature control zone is configured to control the temperature of the interior of the housing. Alternatively, the injection mechanism can be selected from a group consisting of T-injection, electro-kinetic injection, and pipette injection. Alternatively, the capillary array can be flat. Alternatively, the capillary array can include a single bend. Alternatively, the housing can be positioned vertically. Alternatively, the housing can be positioned horizontally. Alternatively, the injection mechanism can be mounted to the housing. Alternatively, the housing can be a hard shell housing. Alternatively, the housing can be a flexible polymer housing.

In an alternative embodiment, the housing further comprises a top plate and a base plate. The base plate can comprise a plurality of grooves configured to accommodate the capillary array.

In another embodiment of the present disclosure, an apparatus is provided for conducting a capillary electrophoresis assay. The apparatus can comprise a capillary array comprising an anode end, the capillary array provided in a housing further comprising a reservoir configured to house a separation medium and an anode buffer. The apparatus can also comprise an injection mechanism configured to deliver sample to the capillary array, and a temperature control zone, wherein the temperature control zone is configured to control the temperature of the interior of the housing. Alternatively, the capillary array can further comprise a cathode end. The cathode end can be provided outside the housing, and can be configured to deliver a sample to the capillary array.

In another embodiment, a method is provided for conducting biological analysis of a sample. The method comprises providing a biological analysis device comprising a capillary cartridge, a buffer source, an electrode, an injection mechanism and an injection tip, the cartridge comprising a capillary array, a polymer source, and an injection volume space, wherein the electrode has an anode end and a cathode end. The method can further comprise charging polymer from the polymer source into the capillary array to fill the array. The method can further comprise activating the electrode to pull sample through the injection tip into the injection volume space. The method can further comprise deactivating the electrode. The method can further comprise inserting the injection tip into the buffer source. The method can further comprise conducting biological analysis of the sample.

Alternatively, the injection mechanism can be an electro-kinetic injection mechanism. Alternatively, the injection volume space can be adjacent a sample inlet end of the capillary array. Alternatively, the electrode cathode end can be adjacent a sample inlet side of the capillary array. Alternatively, the electrode anode end can be adjacent a polymer inlet side of the capillary array.

BRIEF DESCRIPTION OF THE FIGURES

FIGS. 5A-5C depict a capillary array design in accordance with various embodiments of the present disclosure.

FIGS. 11A-11C illustrate different views of the horizontal capillary array cartridge of FIG. 10 in accordance with various embodiments of the present disclosure.

DETAILED DESCRIPTION OF THE EMBODIMENTS

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

It should also be recognized that the methods, apparatuses and systems described herein may be implemented in various types of systems, instruments, and machines such as biological analysis systems. For example, various embodiments may be implemented in an instrument, system or machine that performs capillary electrophoresis (CE) on a plurality of samples.

Figure 1:
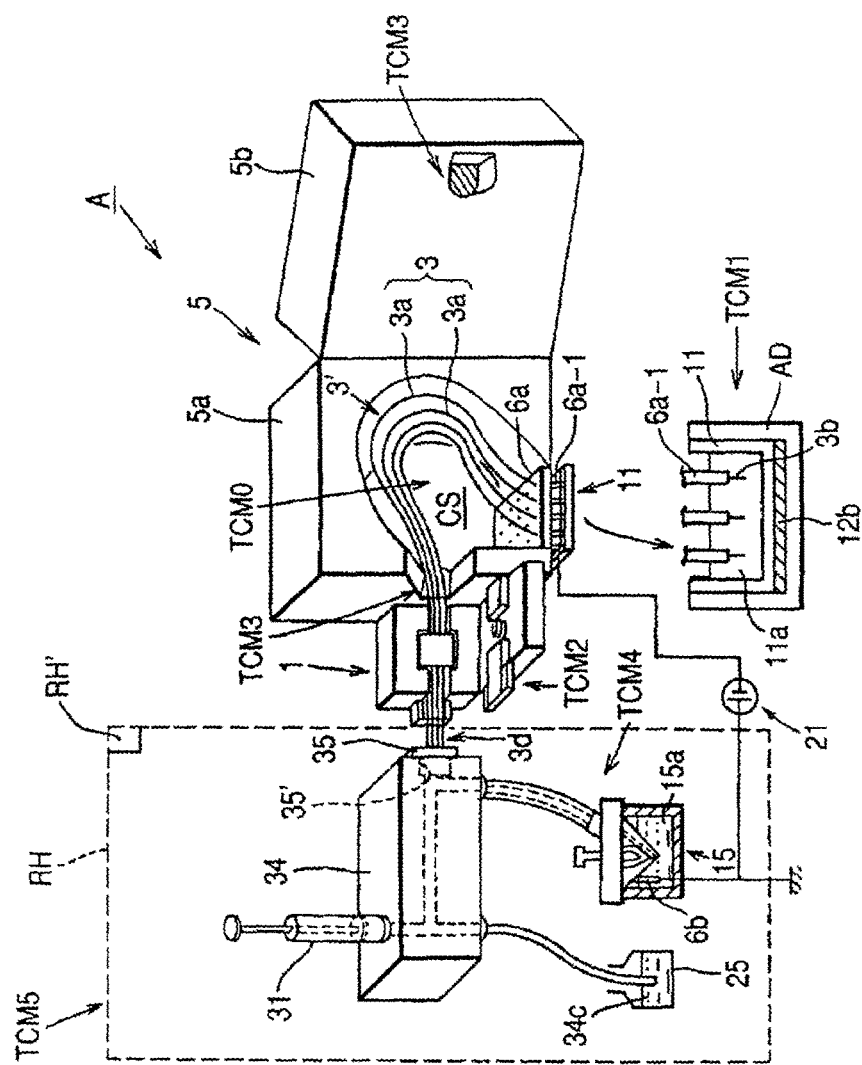
FIG. 1 illustrates a multi-structure capillary electrophoresis device, illustrating multiple temperature control zones TCM0 to TCM5.
Figure 2:
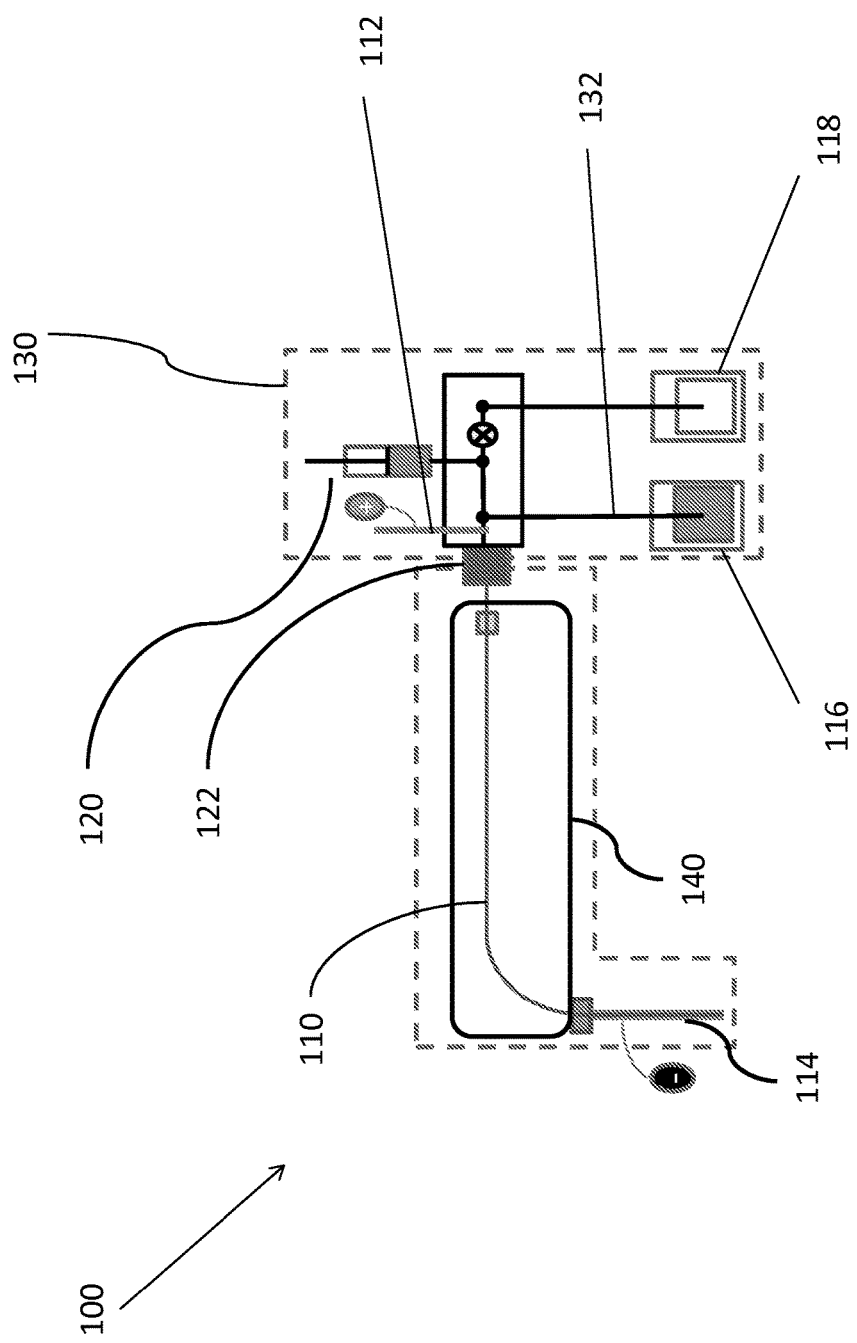
FIG. 2 illustrates a schematic representation of a portion of a conventional capillary electrophoresis apparatus.

FIG. 2 provides a basic schematic representation of a portion of a conventional capillary electrophoresis apparatus 100. In particular, FIG. 2 illustrates a capillary array assembly 110, electrode components (including anode 112 and cathode 114), a polymer source 116, a buffer source 118, and polymer introduction mechanism 120 (illustrated as a syringe pump). As illustrated, a coupling 122 is provided to connect the capillary array assembly 110 to a Polymer/Buffer structure 130, which includes the polymer source 116, buffer source 118, anode 112, and syringe pump 120. As provided, a temperature-controlled zone 140 controls only the enclosed capillary array assembly 110 and cathode 114. As such, additional temperature control is needed for the polymer source 116 and delivery path 132. Moreover, a user must couple the capillary array assembly to the Polymer/Buffer structure 130.

Figure 3:
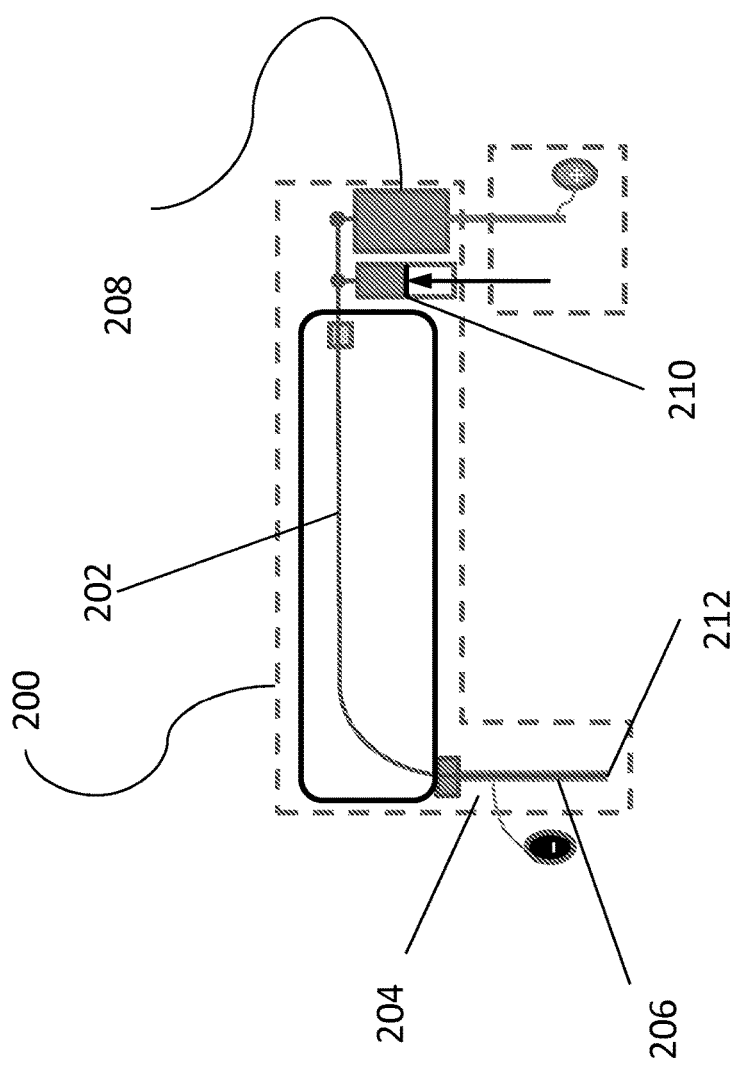
FIG. 3 illustrates a schematic representation of a cartridge according to embodiments of the present disclosure.

Referring to FIG. 3, in certain embodiments, a basic schematic representation of a cartridge 200 is provided that comprises a capillary array 202, a cathode 204, an electrode sleeve 206, a polymer/buffer source 208, and a polymer introduction mechanism 210 (illustrated as a syringe pump). In so doing, the cathode end of the capillaries can be provided outside the cartridge. This exists so that cathode capillary ends 212 can move from the sample (for loading of sample to capillary) (not pictured) to buffer (for insertion of the cathode end into the buffer) (not pictured).

Providing the capillary array 202, cathode 204, polymer/buffer source 206, and polymer introduction mechanism 210 into a single cartridge 200 has many advantages. For example, such a single cartridge 200 allows for removing the buffer by using the polymer as the anode buffer and providing this polymer/buffer package 208 in a small volume to fit into the cartridge and therefore make it a low use item. The polymer/buffer reservoir 208 can advantageously be attached to the array 202 at time of cartridge manufacture so the customer only has to install the entire cartridge into the capillary electrophoresis apparatus. Alternatively, the cartridge can be designed such that the customer only has to attach the polymer/buffer reservoir 208 to the array 202 once before closing and installing the cartridge such that the two are combined for the life of the array and the polymer. These and other advantages will be discussed in further detail.

Specific elements of the cartridge, and associated advantages, follow below.

Figure 4:
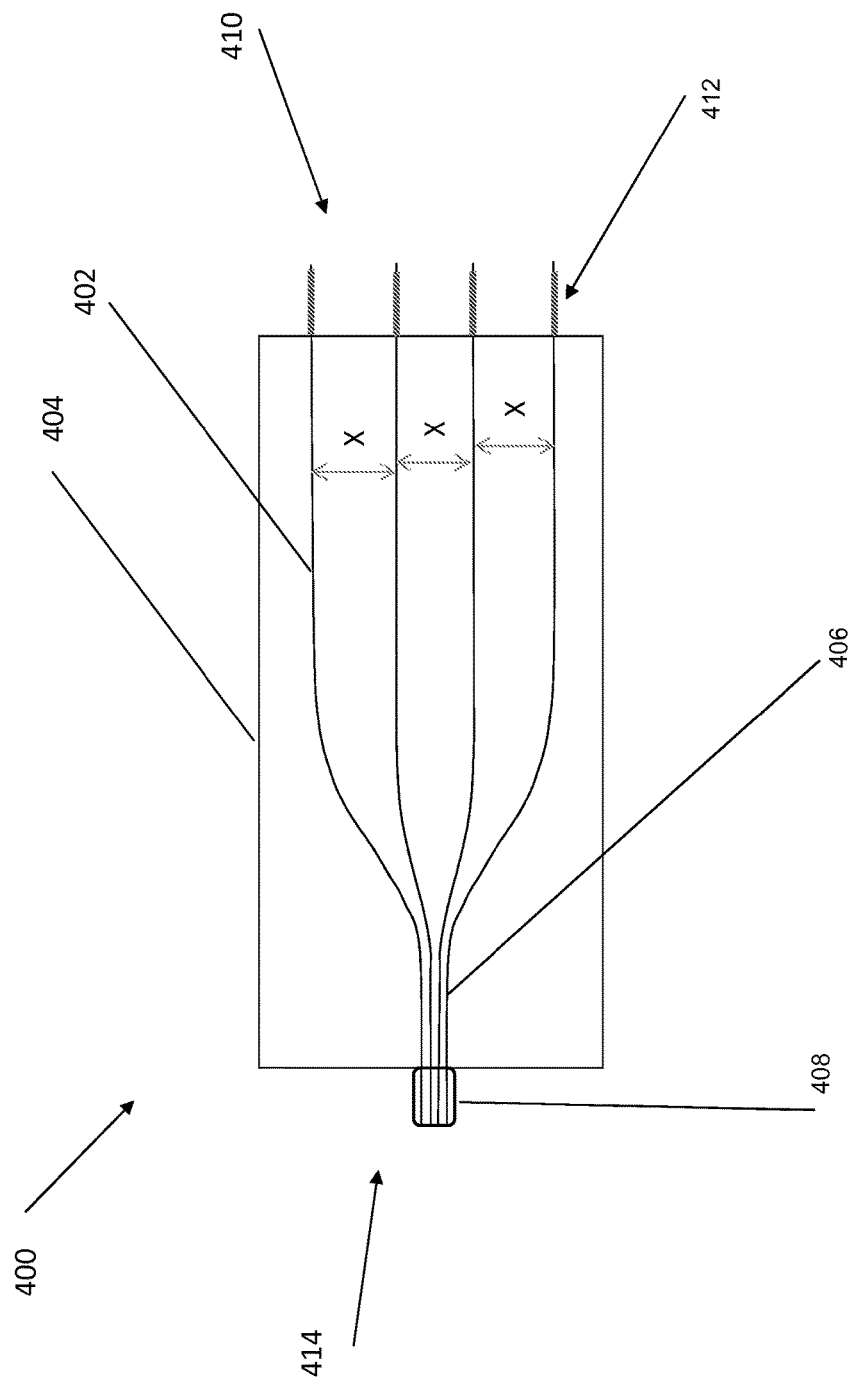
FIG. 4 depicts a capillary array cartridge design in accordance with various embodiments of the present disclosure.

FIG. 4 depicts a capillary array cartridge design in accordance with various embodiments. FIG. 4 illustrates, by way of example, a 4-capillary array cartridge 400 comprising a capillary array 402 and a holder cartridge 404. The holder cartridge is illustrated as rectangular but can have any design that sufficiently houses the capillary array. The capillary array can be assembled independently of the holder. The holder cartridge guides the shape of the individual capillaries in the array within the cartridge assembly such that sample inlet end 410, a detector region 406, and a high-pressure polymer inlet end 414 are formed. The capillaries can be kept in place by being inlaid into groves (described below) in the base plate (described below) of the holder matching the capillary width. The holder can comprise, for example, a non-conductive material such as a heat resistant, low fluorescence plastic, alumina, ceramic or glass.

FIG. 4 also provides the capillary array 402 protruding from the cartridge at a sample inlet 410 (adjacent sleeve electrodes 412) and the opposite polymer pressure-fill end 414 (adjacent a high-pressure fitting connector 408) respectively. The FIG. 4 cartridge has a flat, rectangular shape, and can operate in a vertical orientation with samples presented in, for example, tubes arrayed in a micro-plate, with sample injected from below the cartridge thru the illustrated linear array of capillaries/electrodes protruding from the sample inlet end of the cartridge.

The cartridge design of FIG. 4 also provides slight swivels (not shown) in the path of the non-peripheral capillaries to maintain equal separation distance X (injection to detection). The capillary-to-capillary distance X at the sample injection end 414 of the illustrated cartridge can be configured depending on the micro-plate type holding the sample. For example, for a standard 384-well sample micro-plate, the capillary-to-capillary distance at the sample injection end can be 4.5 mm (compatible w/ standard 384-well micro-plate format) and closest pack (approx. 0.360 mm capillary center-to-center) at the detector and polymer gel block pressure end. Again, the capillary-to-capillary distances at either end can be greater or lesser depending on the sample plate format and dimensions. The distances at either end, however, can further depend on, for example, the cartridge design and dimensions, the number of capillaries, and the detector region.

FIGS. 5A-5C depict a capillary array 500 in accordance with various embodiments. The capillary array comprises a plurality of square flexible fused silica capillaries 502 that can be individually fitted with injection-needle shaped stainless steel electrodes to perform electro-kinetic sample injection (discussed in more detail below). Injections ends of individual capillaries can be glued into the inner bore of a stainless steel sleeve that serves as inlet electrode for electro-kinetic sample injection. This allows for repeated, simultaneous injection of samples. At the polymer gel block, the high-pressure-end of the capillary array 500 is shaped to a ribbon fixed inside a high pressure, rectangular connector 504 (see FIG. 5A) allowing the introduction of viscous solutions of sieving polymer from the polymer gel block into the array via high pressure. All capillaries in the array assembly are of generally equal length, as measured from the injection electrode to the end of the capillary in the gel block fitting. For example, a 10 cm total capillary length may correspond to an 8 cm injection-to-detection capillary array length.

Referring again to holder cartridge 404 of FIG. 4, the holder cartridge can have a flat rectangular layout with a backside base plate 506 (see FIG. 5B). The base plate can be placed against a temperature controlled heater/cooler (not shown) designed to achieve the temperatures necessary for polymer gel separation of sequencing fragments and alternatively to support sub-ambient temperature separations such as single-strand conformation polymorphism (SSCP). The base plate can be thick relative to a thin top plate or cartridge plate 508 (see FIG. 5B) allowing for more optimal optical viewing.

The cartridge 404 can perform injection out of any standard micro-plate including, but not limited to, a 96, 384 and 1536-well micro-titer plates. For example, capillary-to-capillary pitch at the injection end can be configured to be compatible with the standard 384-well plate (for example, a 4.5 mm pitch) or 1536-well plate (for example, 2.2 mm pitch).

The total width of the cartridge, like the capillary pitch, can be determined for example, among other factors, by the number of capillaries in the array and the sample plate format. Again, for a standard 384 well micro-plate, each capillary distance held at the standard 4.5 mm pitch, a 4-capillary cartridge could be, for example, a minimum of approximately 4×4.5=18 mm wide. The length of the cartridge is substantially determined by the length of the capillary. For example, the cartridge for an 8 cm separation distance array can be to be approximately 10 cm long, taking into account the protruding ends.

Note that, due to the flat optical interfaces present in cartridge 404 of FIG. 4, no refractive index matching liquid will be required for detection. Moreover, a notch cutout in top plate 508 of FIG. 5B can allow for direct optical access of the detection system to the capillary ribbon in the detection region 406.

Referring again to cartridge 404 of FIG. 4, the polymer/buffer structure of the instrument (see polymer/buffer structures of FIGS. 2 and 3) can connect to polymer end 414 of the cartridge via a high-pressure connector nozzle 408 protruding from the cartridge. Given to a vertical orientation, the hydrodynamic pressure between the top and the bottom of the cartridge during operation can be balanced by way of lines attached to the polymer/buffer structure leading to an anode reservoir that is level with the cathode buffer reservoir during electrophoresis.

Referring to FIG. 5C, the cartridge can be manufactured to include grooves 510 directing the capillary paths. These grooves can be cut into base plate 506 via standard microfluidics chip technologies such as, for example, micromachining, etching or embossing and after inlay of the capillary array, sealed (fused) with a top plate. Alternatively, an adhesive layer with channel cut out conforming to the capillary paths may be sandwiched between base plate 506 (e.g., glass base plate) and top plate 508 to achieve the same capillary path effect.

The cartridge components and designs illustrated in FIGS. 4 and 5, in accordance with various embodiments, has many advantages. One advantage is the assembly of capillary array 500 can be modular 404 and separate from cartridge holder manufacture. Another advantage is the cartridge allows for use with a higher density sample tube format, thus allowing for smaller sample sizes, more compact designs, a smaller footprint of the sample tray and, as a result, a smaller capillary electrophoresis apparatus.

A flat cartridge design, whether vertically or horizontally oriented, when combined with an appropriate sample injection mechanism (for example, pipette injection, T-injection and electro-kinetic injection discussed in more detail below) eliminates excessive capillary bends or curved paths in the injection-to-detection region needed so that the cathode end of the array can dip into the sample, tube or well plate. Bends in the capillary can cause increased band dispersion and thus can affect quality of results. Even with designs where capillaries are curved to address the sample, the use of a single bend for that purpose can still be advantageous. Moreover, building the curve into the cartridge with a hard-shell can advantageously prevent the customer from having to bend the capillary.

A flat capillary or channel can also eliminate any height differences between the anode and cathode buffers. Height differences can cause siphoning of the polymer that leads to band broadening and, again, can affect quality of results.

The following FIGS. 6-14 illustrate further embodiments of a cartridge, which further include an embedded polymer/buffer structure (e.g., reservoir).

Figure 6:
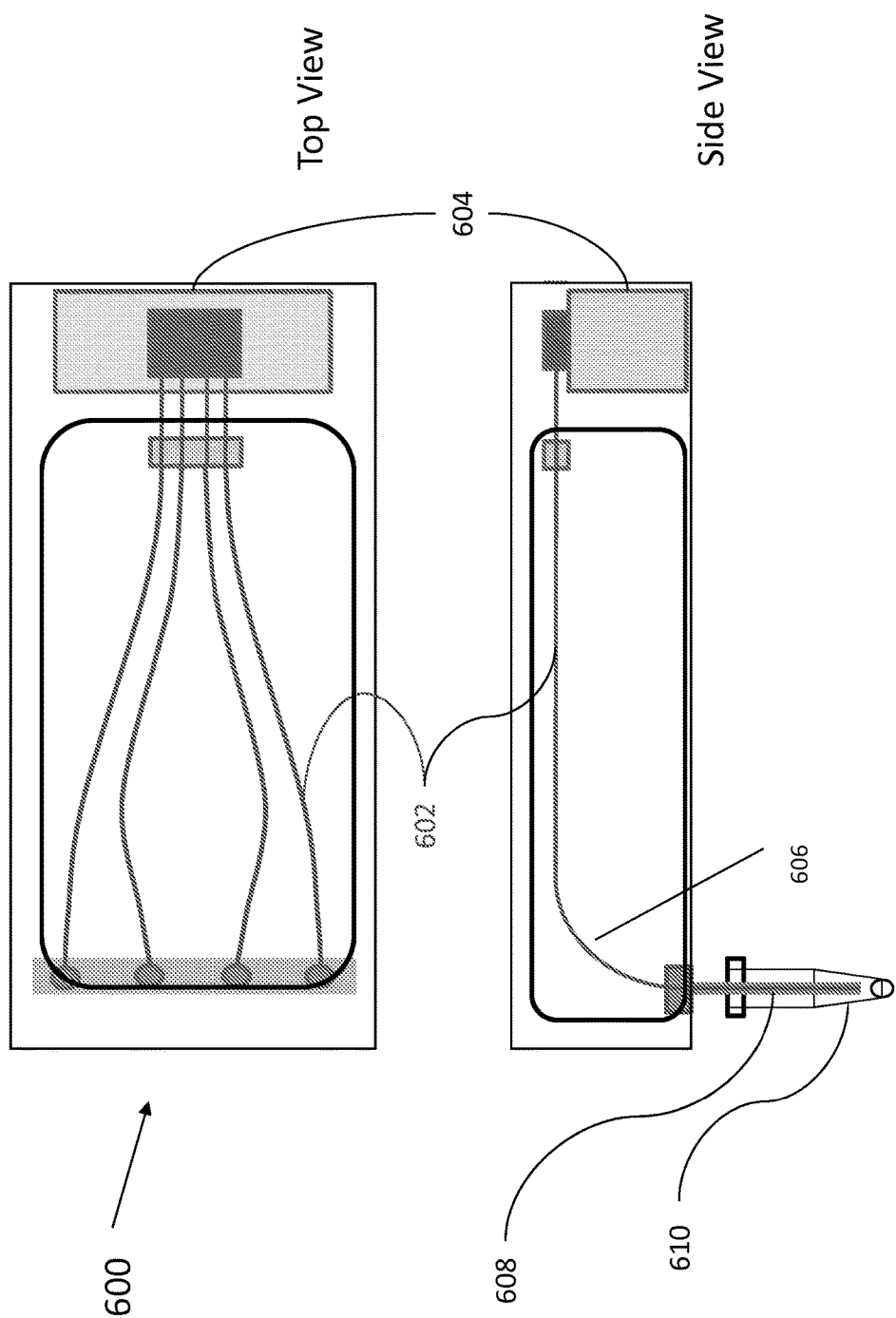
FIG. 6 depicts schematic interior side and top views of a horizontal capillary array cartridge in accordance with various embodiments of the present disclosure.
Figure 7:
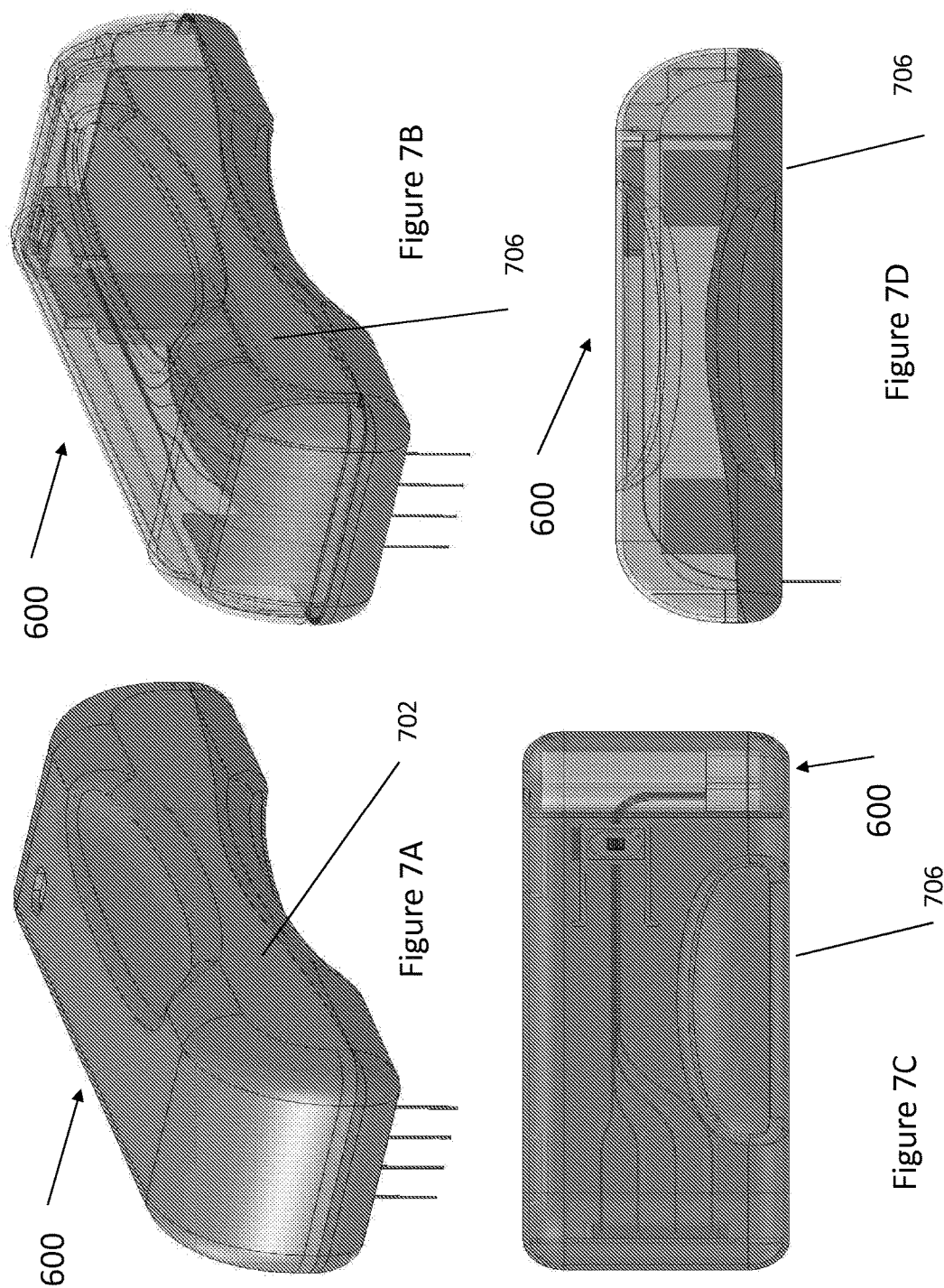
FIGS. 7A-7D illustrate different views of the horizontal capillary array cartridge of FIG. 6 with an exterior hard-shell in accordance with various embodiments of the present disclosure.

FIG. 6 depicts a schematic interior side and top views of horizontal capillary array cartridge 600 in accordance with various embodiments. The cartridge comprises a capillary array 602 and a polymer/buffer reservoir 604, where the polymer can serve both as a polymer for the capillaries and an anode buffer. The cartridge includes a single bend 606 in the injection-to-detection region to allow access of the sample inlet/cathode end 608 to a sample source 610 for loading. Access also can allow for a capillary cleaner (e.g., water) and a buffer for electrophoresis. The cartridge, by its design, provides temperature control of at least 80% of the capillary path.

FIGS. 7A-7D illustrates different views of the horizontal capillary array cartridge 600 of FIG. 6 with an exterior hard-shell 702. FIG. 7A is a perspective view of the horizontal capillary array cartridge 600 with the cartridge shell 702 and exposed cathode side capillary ends 704. FIG. 7B is a perspective view with a transparent cartridge shell 706. FIG. 7C is a top view of transparent cartridge shell 706. FIG. 7D is a side view transparent cartridge shell 706.

Figure 8:
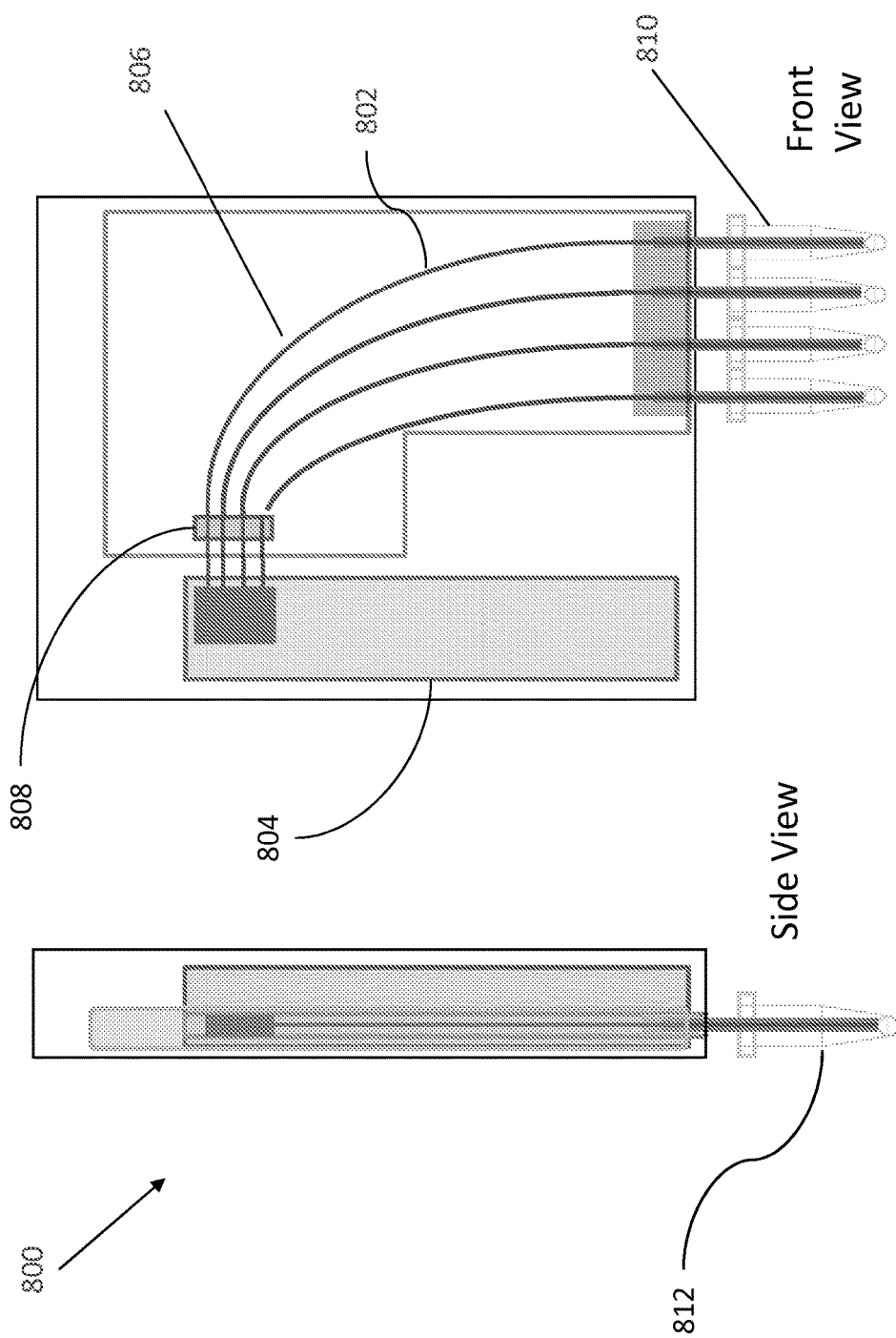
FIG. 8 depicts schematic interior side and front views of a vertical capillary array cartridge in accordance with various embodiments of the present disclosure.
Figure 9:
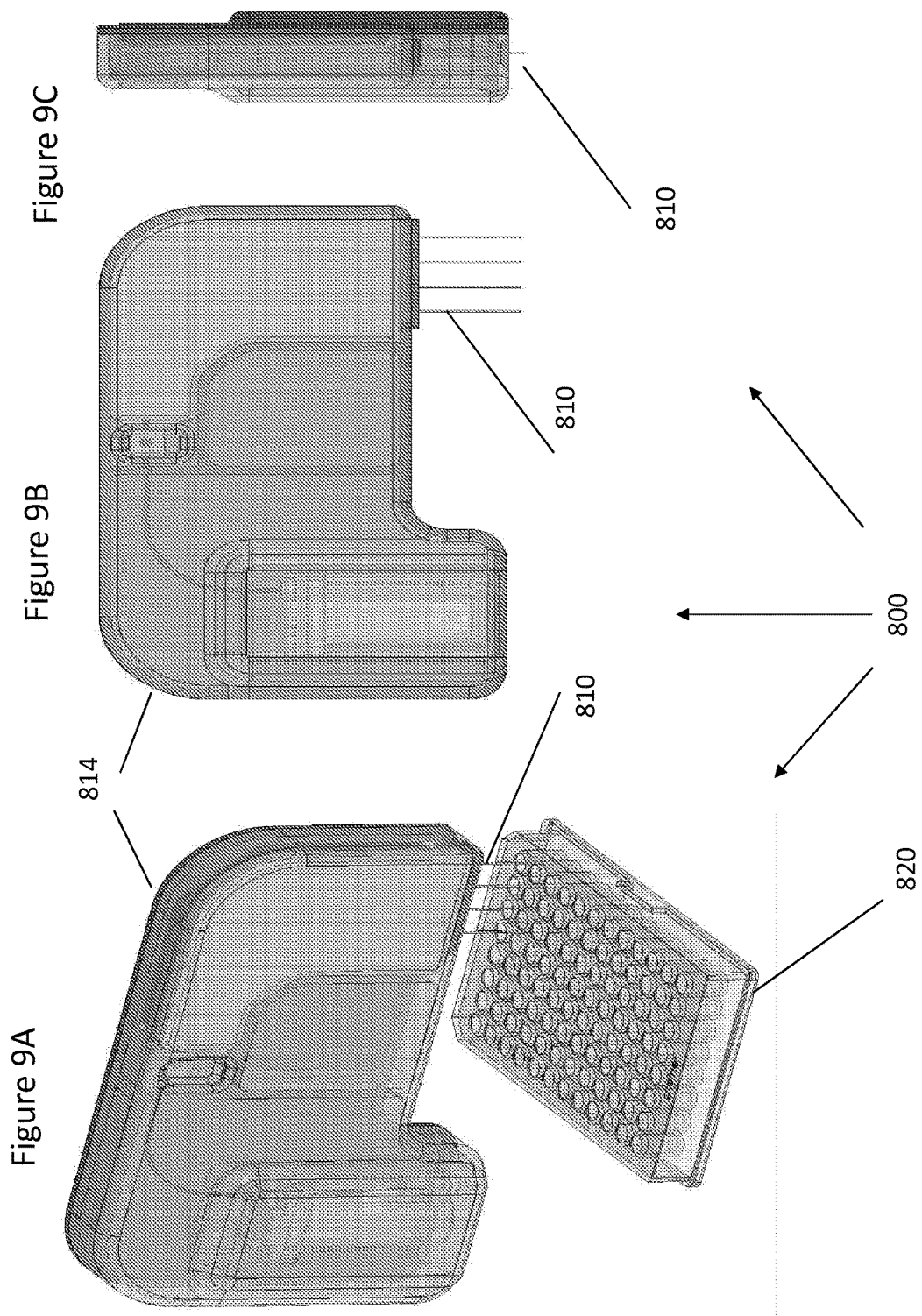
FIGS. 9A-9C illustrate different views of the vertical capillary array cartridge of FIG. 8 with an exterior hard shell in accordance with various embodiments of the present disclosure.

FIG. 8 depicts schematic interior side and front views of a vertical capillary array cartridge 800 in accordance with various embodiments. The cartridge comprises a capillary array 802 and a polymer/buffer reservoir 804, where the polymer serves both as a polymer for the capillaries and an anode buffer. The cartridge includes a single bend 806 in the injection-to-detection region to allow orientation with an optical detection region 808 while providing access of a sample inlet/cathode end 810 to a sample source 812 for loading. Access also can allow for a capillary cleaner (e.g., water) and a buffer for electrophoresis. The cartridge, by its design, provides temperature control of at least 80% of the capillary path.

FIGS. 9A-9C illustrate different views of the vertical capillary array cartridge 800 of FIG. 8 with an exterior hard-shell. FIG. 9A is a perspective view of the vertical capillary array cartridge with a transparent cartridge shell 814 and the exposed sample inlet/cathode capillary ends 810 adjacent wells of a 96 well micro-plate 820. FIG. 9B is a front view with a transparent cartridge shell 814. FIG. 9C is a side view of transparent cartridge shell 814.

Figure 10:
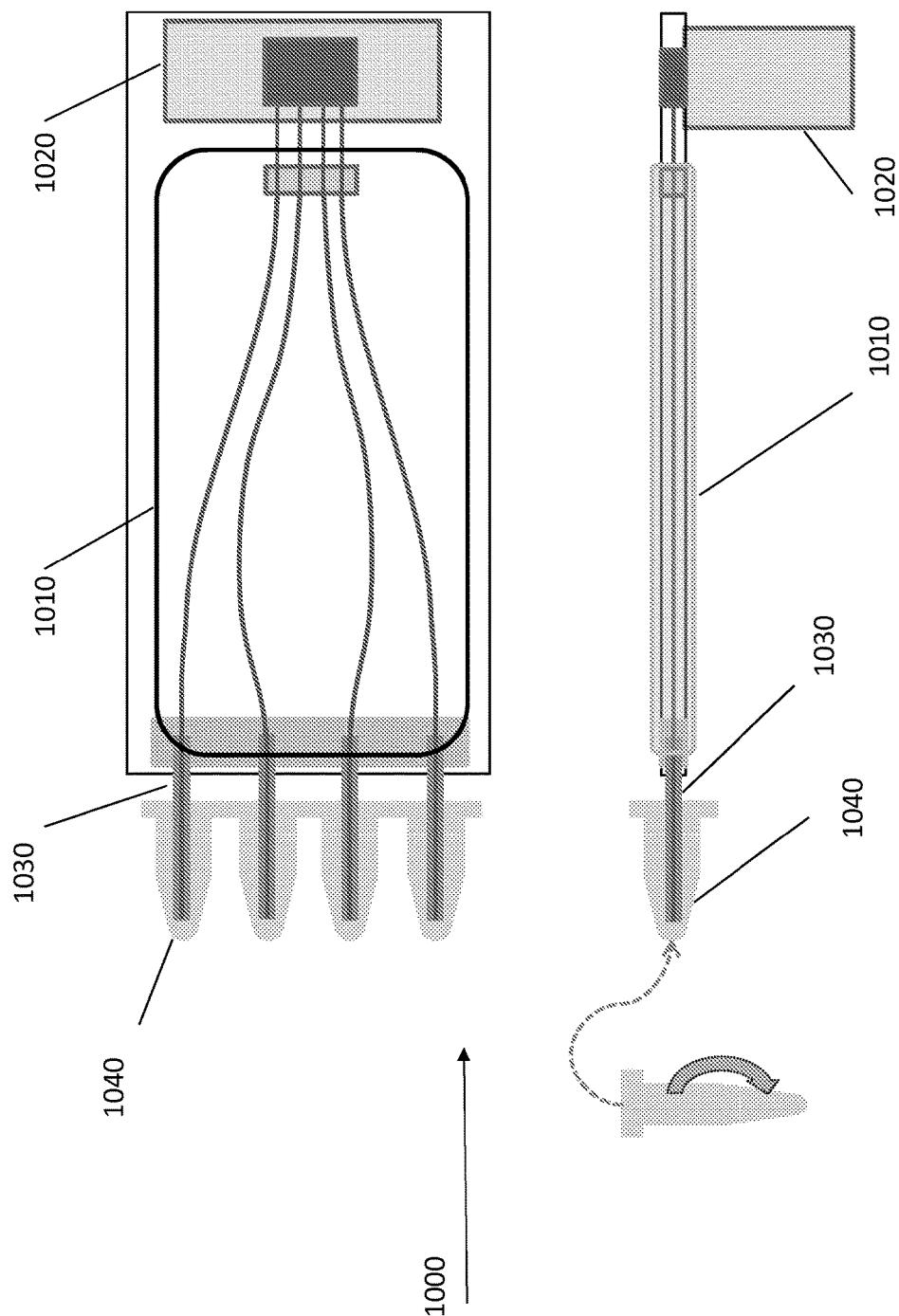
FIG. 10 depicts interior views of a horizontal capillary cartridge in accordance with various embodiments of the present disclosure.

FIG. 10 depicts schematic interior views of a horizontal capillary array cartridge 1000 in accordance with various embodiments. The cartridge comprises a capillary array 1010 and a polymer/buffer reservoir 1020, where the polymer serves both as a polymer for the capillaries and an anode buffer. The cartridge includes a flat capillary path (see side view) while still providing access of sample inlet/cathode end 1030 to a sample source 1040 for loading. Access also allows for a capillary cleaner (e.g., water) and a buffer for electrophoresis. By providing a flat capillary path with no bend in the injection-to-detection region to access samples, the cartridge can access samples from a sample well plate having a vertical orientation. The cartridge, by its design, provides temperature control of at least 80% of the capillary path.

FIGS. 11A-11C illustrate different views of horizontal capillary array cartridge 1000 of FIG. 10 with an exterior hard-shell and casing to protect the exposed sample inlet/cathode end 1030 of the capillaries. FIG. 11A is a perspective view of the horizontal capillary array cartridge with a cartridge shell 1050. FIG. 11B is a front view with a transparent cartridge shell 1060. FIG. 11C is a side view of transparent cartridge shell 1060.

Figure 12C:
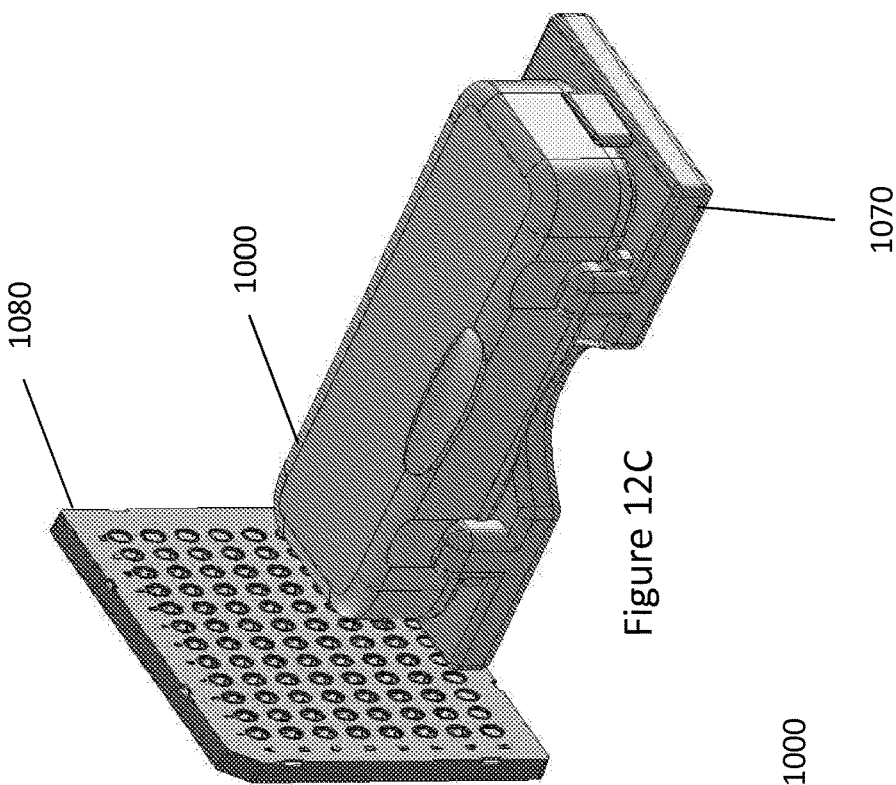
FIGS. 12A-12C illustrate the hard shell horizontal capillary array cartridge of FIGS. 11A-11C installed on a base plate in accordance with various embodiments of the present disclosure.
Figure 12A:
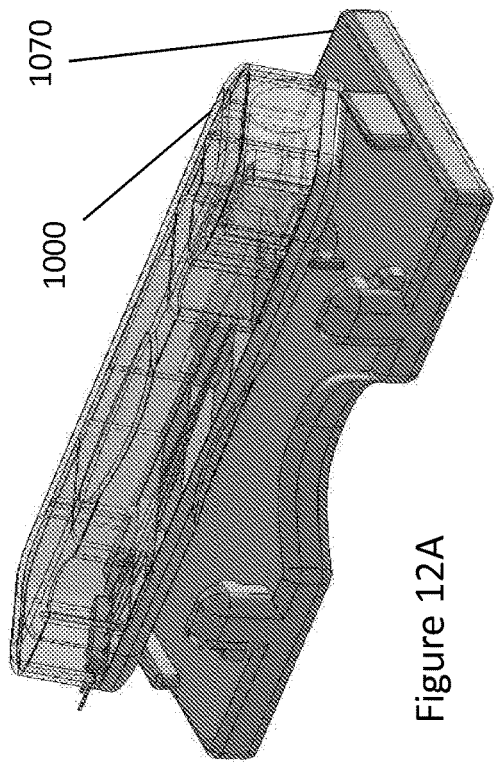
Figure 12B:
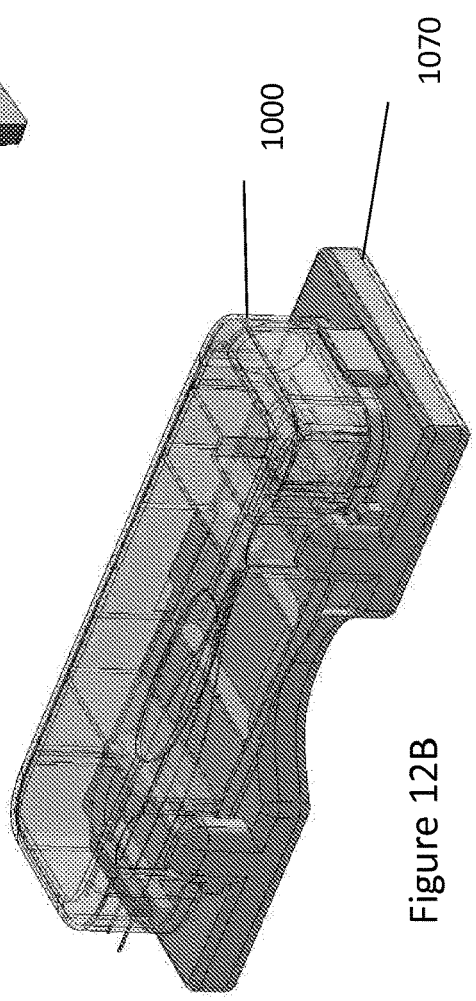

FIGS. 12A-12C illustrate hard-shell horizontal capillary array cartridge 1000 of FIGS. 11A-11C installed on a base plate 1070. FIG. 12A is a perspective view of horizontal capillary array cartridge 1000 prior to registration with base plate 1070. FIG. 12B is a perspective view of the horizontal capillary array cartridge after attachment to the base plate. FIG. 12C is a perspective view of the combined cartridge/base plate accessing a 96-well micro-plate 1080.

Figure 13:
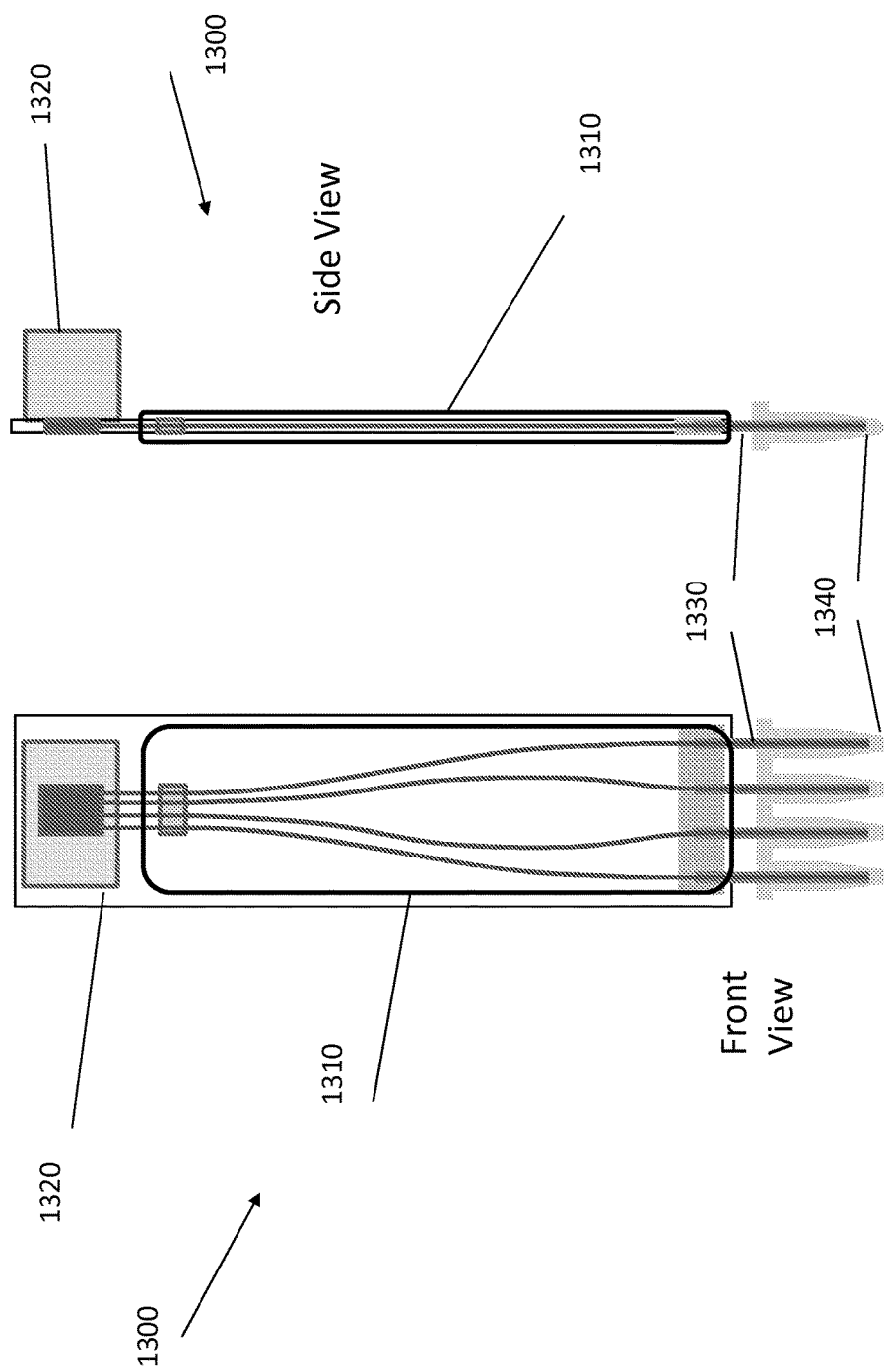
FIG. 13 depicts a schematic interior view of a vertical capillary array cartridge in accordance with various embodiments of the present disclosure.
Figure 14:
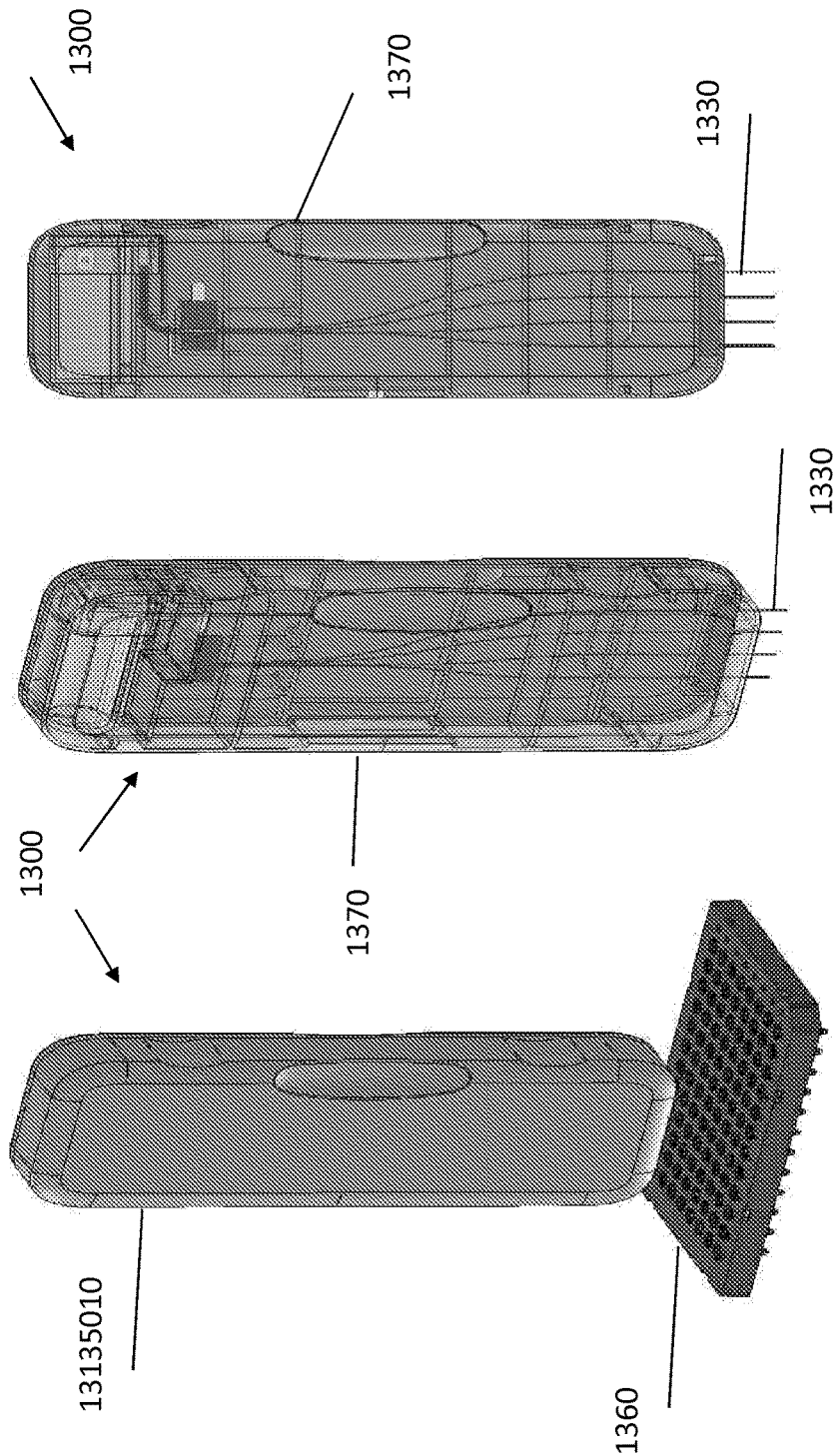
FIGS. 14A-14C illustrate different views of the vertical capillary array cartridge of FIG. 13 in accordance with various embodiments of the present disclosure.

FIG. 13 depicts schematic interior views of a vertical capillary array cartridge 1300 in accordance with various embodiments. The cartridge comprises a capillary array 1310 and a polymer/buffer reservoir 1320, where the polymer serves both as a polymer for the capillaries and an anode buffer. The cartridge includes a flat capillary path (see side view) while still providing access of a sample inlet/cathode end 1330 to a sample source 1340 for loading. Access also allows for a capillary cleaner (e.g., water) and a buffer for electrophoresis. By providing a flat capillary path with no bend in the injection-to-detection region to access samples, the cartridge can access samples from a sample well plate below the cartridge. The cartridge, by its design, provides temperature control of at least 80% of the capillary path. For the vertical capillary array cartridge, to keep the polymer from moving down the capillary due to gravity, a pressure control mechanism (not pictured) can be used at the top of the capillary array to prevent a pressure head.

FIGS. 14A-14C illustrate different views of the vertical capillary array cartridge 1300 of FIG. 13 with an exterior hard-shell and the exposed sample inlet/cathode capillary ends 1330. FIG. 14A is a perspective view of the vertical capillary array cartridge 1300 with a cartridge shell 1350 and the exposed sample inlet/cathode capillary ends 1330 adjacent wells of a 96 well micro-plate 1360. FIG. 14B is a perspective view with a transparent cartridge shell 1370. FIG. 14C is a front view of transparent cartridge shell 1370.

Such combined capillary array/polymer source cartridge designs, besides providing the advantages above, advantageously allow for removing the buffer by using the polymer as the anode buffer and providing this polymer/buffer package in a small volume to fit into the cartridge and therefore make it a low use item. Another advantage of including the polymer/buffer reservoir in the cartridge is that, when attached to the array at time of cartridge manufacture, the customer only has to install the entire cartridge into the capillary electrophoresis apparatus. A further advantage is that, even when designed such that the customer only has to attach the polymer/buffer reservoir to the array once before closing and installing the cartridge, the cartridge is used for the life of both the array and polymer such that the whole cartridge can be replaced at once instead of as individual parts. Even further, the combined cartridge advantageously provides a single temperature control zone for capillary and polymer/buffer that is more easily controlled than multi-component/multi-zone devices. This also allows for temperature control of a higher percentage of the capillary path, which in turn keeps the polymer at a constant temperature.

Figure 15:
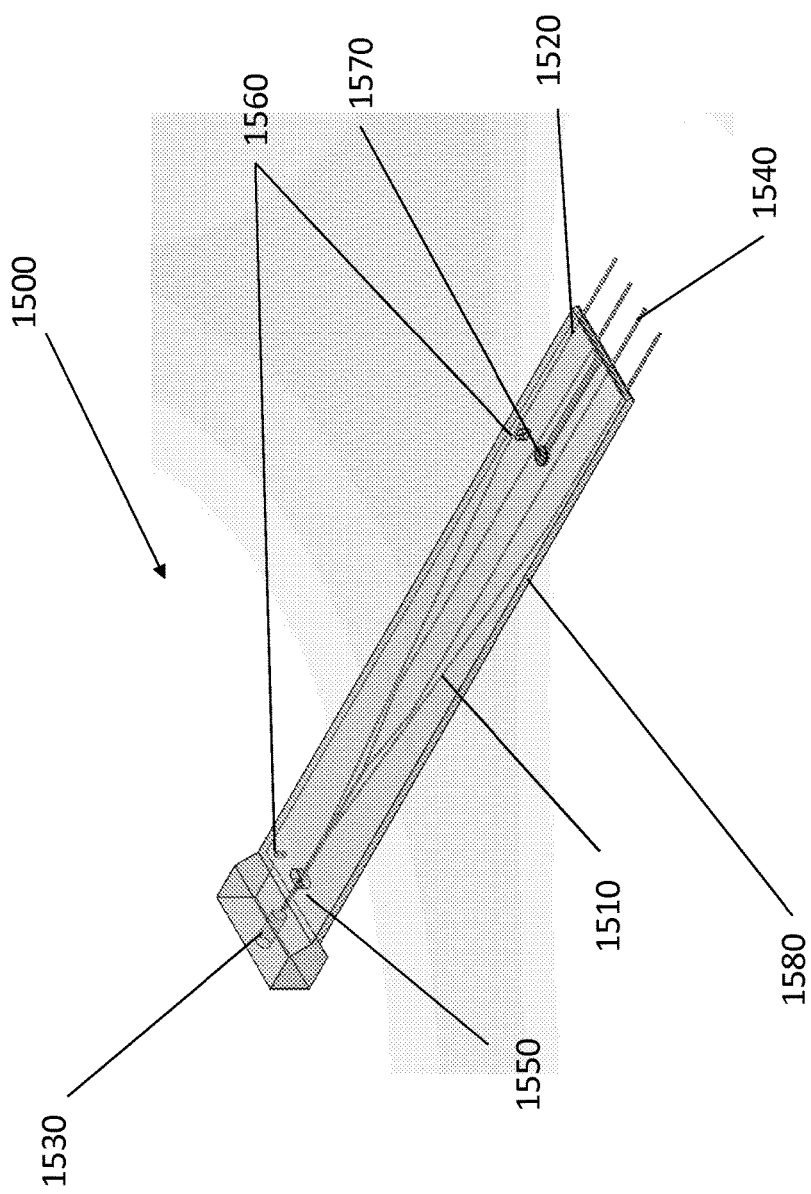
FIGS. 15 and 16 illustrate flexible consumable devices in accordance with various embodiments of the present disclosure.
Figure 16:
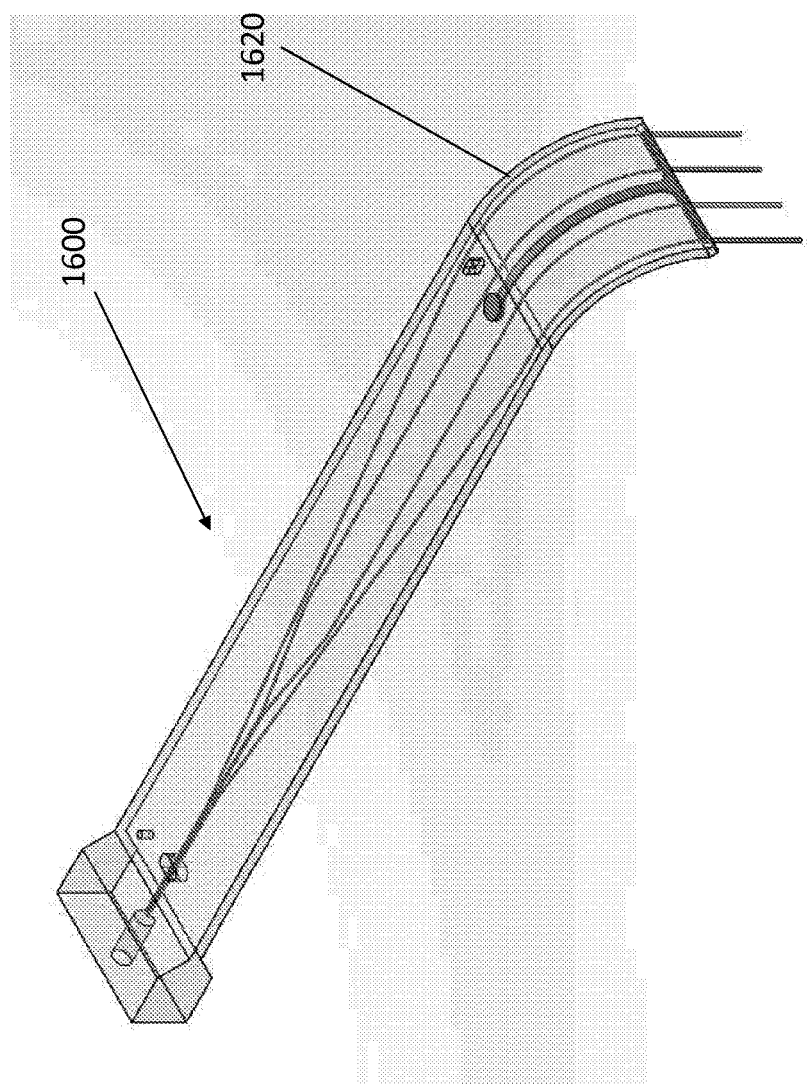

FIGS. 15 and 16 illustrate a flexible consumable device housing multiple capillaries for housing in a capillary electrophoresis apparatus, in accordance with various embodiments. FIG. 15 illustrates a flat flexible consumable device 1500 with a capillary array 1510 having a capillary length extending from a fluidic port 1530 to steel tubing connectors 1540 (discussed below) surrounding sample inlet/cathode capillary ends 1520, which are parallel to the spaced portion of the capillary length. This flat shape can be the shape as shipped to user or the final shape as loaded on a capillary electrophoresis apparatus. Fluidic port 1530 provides access to polymer. A detection window 1550 is provided for optical access. Position alignment features 1560 are provided for registration with a capillary electrophoresis apparatus. Embedded high voltage contacts 1570 and steel tubing terminations 1540 are provided for electro-kinetic sample loading and electrophoresis performance. The consumable can be made from a thermally conductive electrically insulating flexible polymer 1580 to provide the necessary flexibility while providing the desired pliability for flexible use.

FIG. 16 illustrates an example of a loaded curved flexible consumable device 1600, curved to meet a specific required shape commensurate with the design of an associated capillary electrophoresis apparatus. In the case of FIG. 16, the sample inlet/cathode capillary ends 1620 are bent to allow vertical sample loading.

A flexible consumable device provided in a compliant package, such as that illustrated in FIGS. 15 and 16, advantageously meets multiple demands without creating a bulkier arrangement. The consumable can assume any of the capillary orientations illustrated in FIGS. 6-14 (as well as other variants) based on its ability to manipulate to suit user preferences. Moreover, based on the thin design and the materials used, the consumable also lends itself well to heat distribution as well as electrical insulation. Further, the consumable's compliant nature allows it to have both a horizontal portion to avoid hydrostatic pressure differences and vertical portion for sample injection. Even further, the molded structure can be expanded to accommodate an on-board polymer/buffer source to provide a combined flexible consumable design having many of the advantages provided by the combined cartridges discussed earlier.

Figure 17:
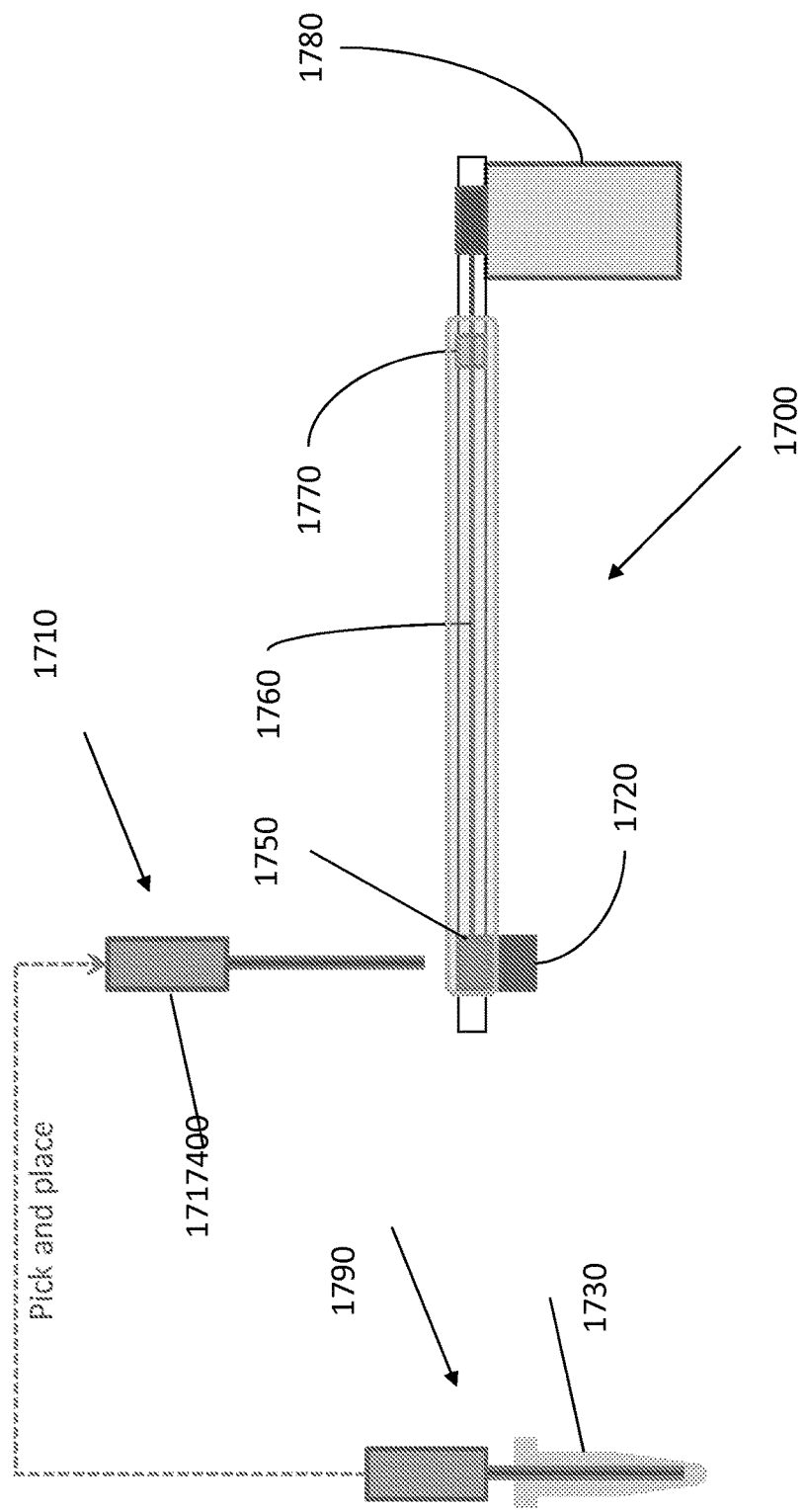
FIG. 17 illustrates a pipette injection mechanism incorporated into a capillary array cartridge in accordance with various embodiments of the present disclosure.

FIG. 17 depicts an example of a pipette injection mechanism 1710 incorporated into a horizontal capillary array cartridge 1700, in accordance with various embodiments. The cartridge, with the pipette injection mechanism, includes an on-board service station 1720 for cleaning the pipette injection mechanism, storage of the pipette injection mechanism, and storage of buffer for use during electrophoresis. The pipette injection mechanism can allow for access, at a remote location 1790, to a sample source 1730. Access can also allow for a capillary cleaner (e.g., water) and a buffer remotely from the cartridge. Pipette injection mechanism 1710 can use any mechanical pump mechanism 1740 to withdraw and inject contents contained therein including, for example, a positive displacement pump. By providing remote access to pipette contents, sample inlet/cathode capillary ends 1750 are not exposed outside cartridge 1700. This allows for complete temperature control of the path of capillary array 1760 from injection-to-detection. Cartridge 1700 of FIG. 17 also includes an optical access 1770 and a polymer/buffer reservoir 1780.

Figure 18:
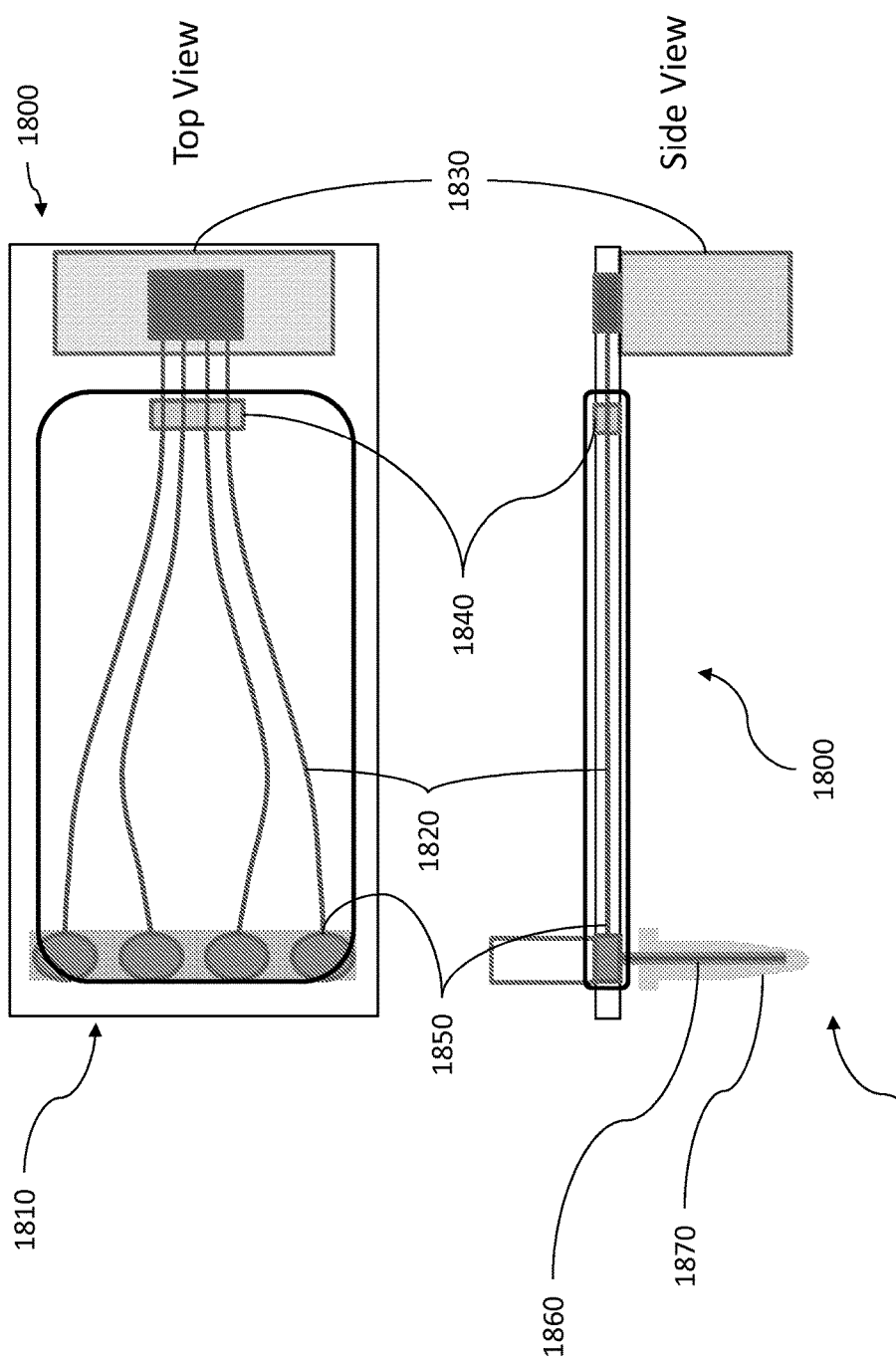
FIGS. 18 and 19 illustrate a T-injection mechanism incorporated into a capillary array cartridge in accordance with various embodiments of the present disclosure.

FIG. 18 depicts an example of a T-injection mechanism 1810 incorporated into a horizontal capillary array cartridge 1800, in accordance with various embodiments. Capillary array cartridge 1800 also includes a capillary array 1820, a polymer/buffer reservoir 1830. An optical detection region 1840, a sample inlet/cathode capillary end 1850, and a cap inlet/tip 1860.

Figure 19:
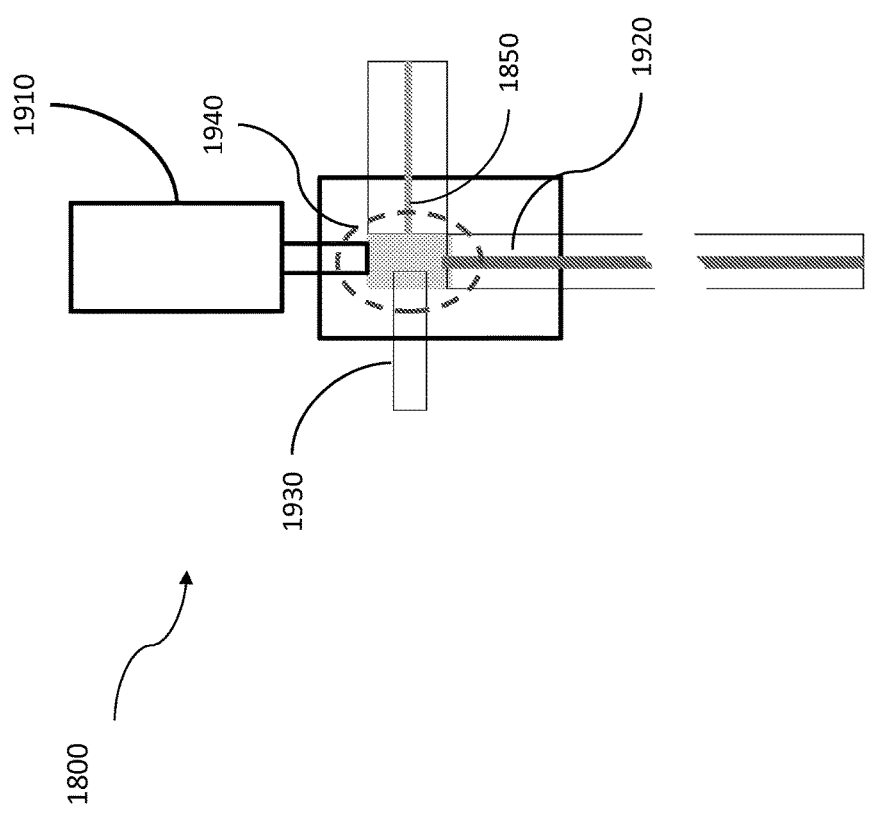

FIG. 19 depicts T-injection mechanism 1810 in more detail. The T-injection mechanism can comprise an injection device 1910 adjacent sample inlet/cathode capillary end 1850, an injection capillary 1920 (optional in electrophoresis) adjacent the sample inlet/cathode capillary end, an electrode 1930, and an injection volume space 1940 intersecting injection device 1910, sample inlet/cathode capillary end 1850, injection capillary 1920 and electrode 1930. The T-injection mechanism can further include a feedback mechanism (not pictured) to sense when sample volume is changed. The injection device, together with the injector capillary, accesses sample, capillary cleaner (e.g., water) or buffer (see element 1870 of FIG. 18) as necessary to perform electrophoresis. The T-injection mechanism can allow access to samples, capillary cleaner (e.g., water) and buffer adjacent cartridge 1800 without exposing sample inlet/cathode capillary ends 1850 to the environment. The T-injection mechanism can use any pump mechanism to withdraw and injection contents contained therein including, for example, a vacuum or syringe pump. The configuration of the T-injection mechanism therefore allows for complete temperature control of the capillary path from injection-to-detection.

Figure 20:
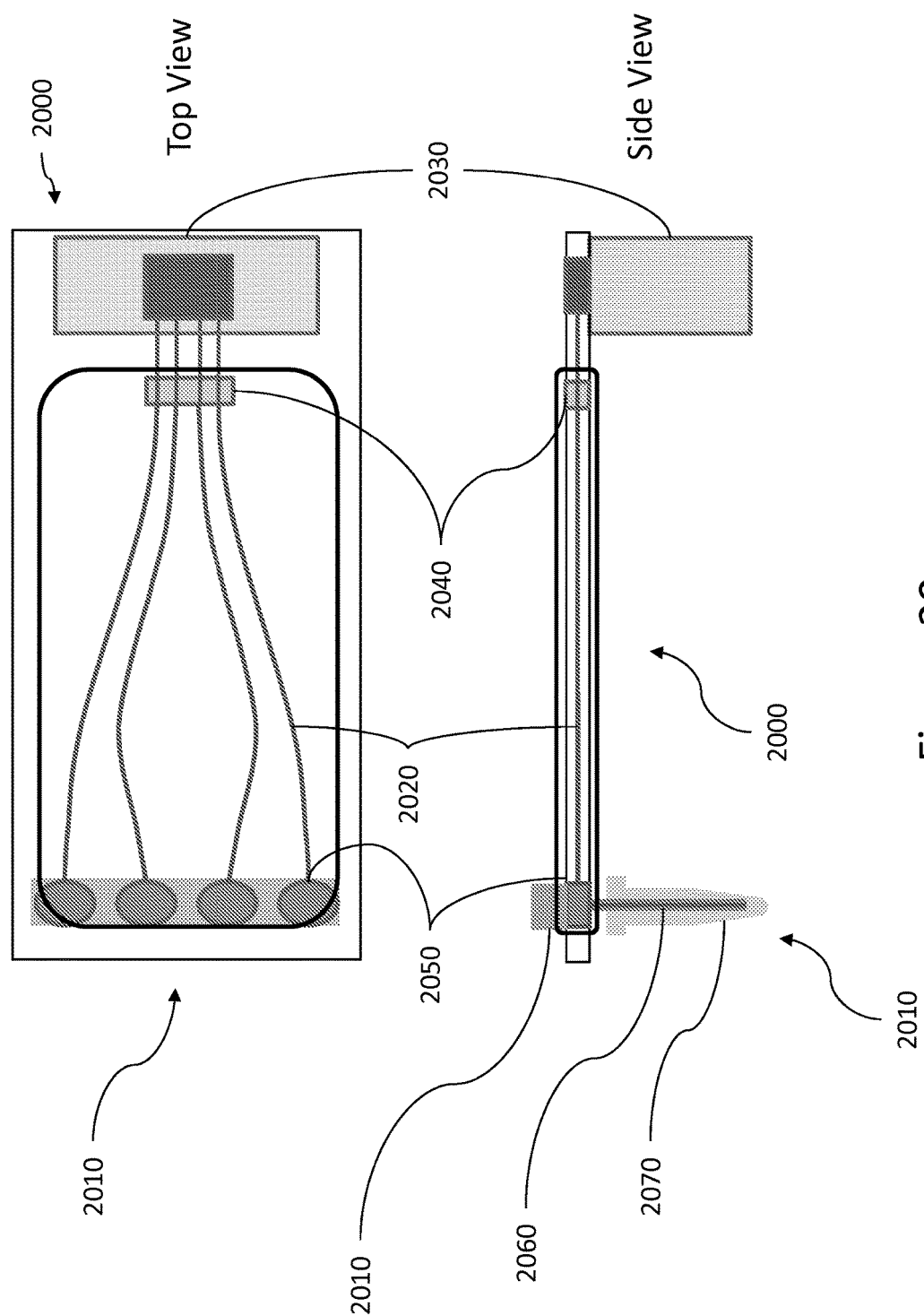
FIGS. 20 and 21 illustrate an electro-kinetic injection (EK) mechanism incorporated into a capillary array cartridge in accordance with various embodiments of the present disclosure.

FIG. 20 depicts an example of an electro-kinetic injection (EK) mechanism 2010 incorporated into a horizontal capillary array cartridge 2000, in accordance with various embodiments. Capillary array cartridge 2000 includes a capillary array 2020, a polymer/buffer reservoir 2030, an optical detection region 2040, a sample inlet/cathode capillary end 2050, and a capillary inlet/tip 2060.

Figure 21:
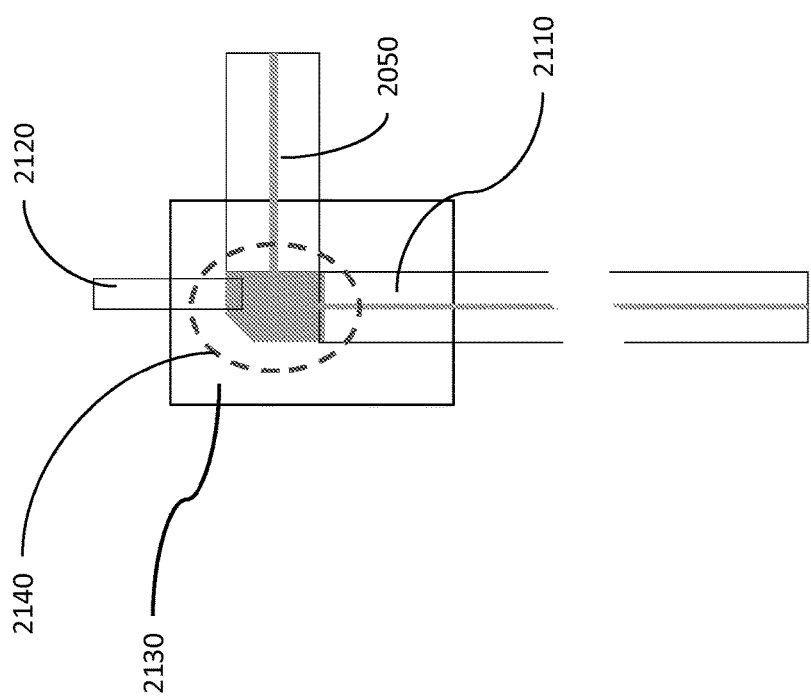

FIG. 21 depicts EK mechanism 2010 in more detail. The EK mechanism can comprise an injection capillary 2110 (optional in electrophoresis) adjacent sample inlet/cathode capillary end 2050, an electrode 2120 for anode-injection, an electromechanical connector 2130 (for example, a MEMs connector), and an injection volume space 2140 intersecting the sample inlet/cathode capillary end 2050, injection capillary 2110 and electrode 2120. The anode-injection electrode, together with the injector capillary, accesses a sample, buffer or capillary cleaner (e.g., water) as necessary to perform electrophoresis (see element 2070 of FIG. 20). The EK mechanism can allow access to samples, capillary cleaner (e.g., water) and buffer adjacent cartridge 2000 without exposing the sample inlet/cathode capillary ends 2050 to the environment. The configuration of the EK mechanism therefore allows for complete temperature control of the capillary path from injection-to-detection.

Figure 22:
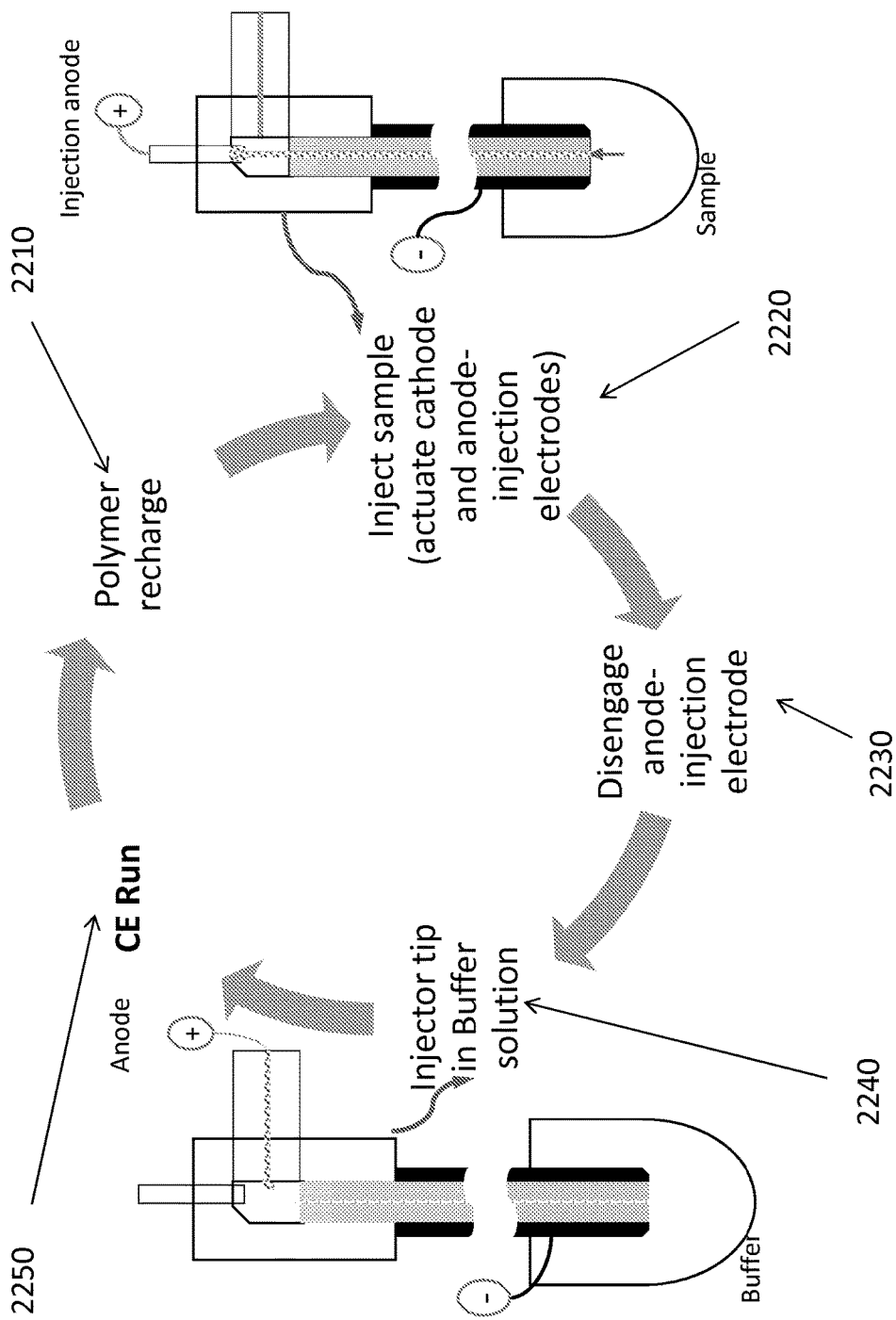
FIG. 22 depict an example capillary electrophoresis workflow in accordance with various embodiments of the present disclosure.

FIG. 22 depicts an example of a capillary electrophoresis (CE) workflow 2200 using an EK mechanism, in accordance with various embodiments. In this example, features of the EK mechanism of FIGS. 20 and 21 will be used for reference only. Starting at step 2210, polymer is recharged into capillary array 2020 to prepare the CE system for a CE run. After polymer fills the array, sample 2070 is ready for loading into injection volume space 2140 of the EK mechanism. At step 2220, activation of cathode and anode-injection electrodes pulls sample into injection volume space 2140 adjacent sample inlet/cathode capillary end 2050 of capillary array 2020. Once sufficient sample volume is loaded into space 2140, anode-injection electrode 2120 is deactivated at step 2230. After deactivating the electrode, injection capillary tip 2060 is inserted into a buffer solution 2070 at step 2240. At this point, a CE run can commence (step 2250).

Figure 23B:
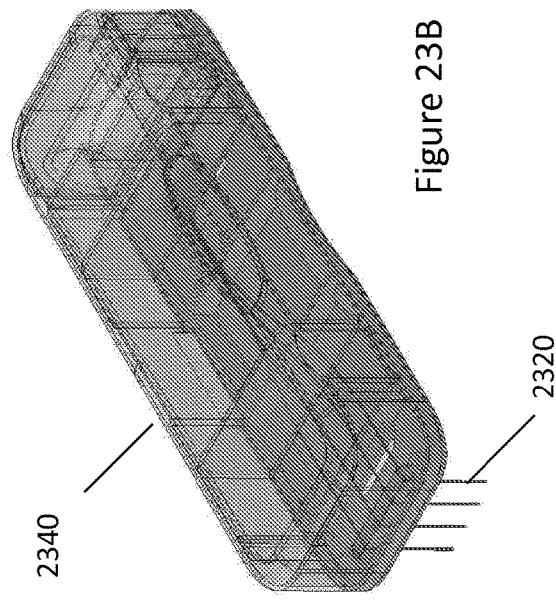
FIGS. 23A-23D illustrate different views of an EK mechanism incorporated in a capillary cartridge according to embodiments of the present disclosure.
Figure 23D:
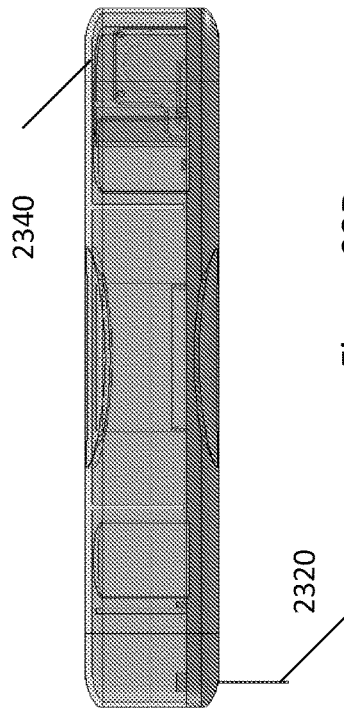
Figure 23A:
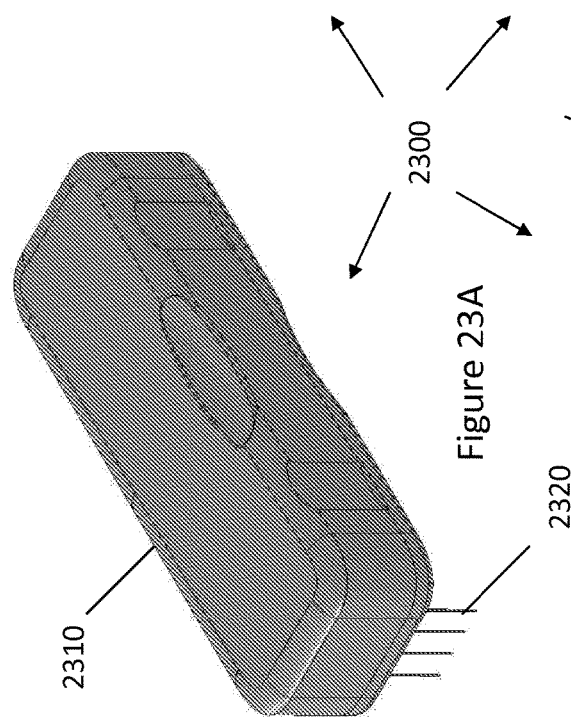
Figure 23C:
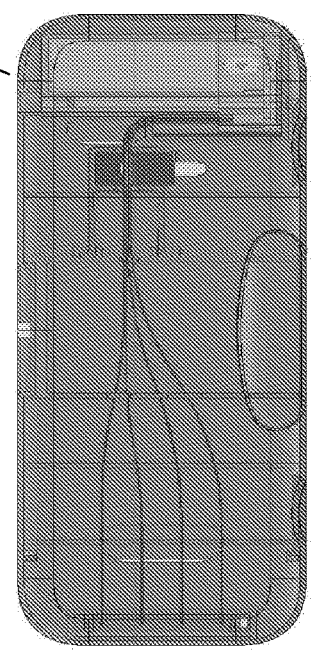

FIGS. 23A-23D illustrate different views of EK mechanism 2010 incorporated into a horizontal capillary array cartridge 2300 with an exterior hard-shell and exposed injection capillary ends, in accordance with various embodiments. FIG. 23A is a perspective view of the horizontal capillary array cartridge 2300 with a cartridge shell 2310 and exposed injection capillary ends 2320. FIG. 23B is a perspective view with a transparent cartridge shell 2340. FIG. 24C is a top view of transparent cartridge shell 2340. FIG. 24D is a front view of transparent cartridge shell 2340.

It should be noted that, while each of the described injection methods are exemplified with a horizontal capillary array cartridge, each of the described injection methods are interchangeable with any of the described capillary array cartridge designs, regardless of shape, design, rigidity or flexibility. Moreover, though each of the cartridge designs of FIGS. 6-14 are depicted with a hard-shell casing, each of these cartridge designs can be encased in any other contemplated casings including, but not limited to, soft-shell casings and flexible polymer moldings.

Various embodiments of the present invention have been described above. It should be understood that these embodiments have been presented by way of example only, and not limitation. It will be understood by those skilled in the relevant art that various changes in form and detail of the embodiments described above may be made without departing from the spirit and scope of the present invention as defined in the claims. Thus, the breadth and scope of the present invention should not be limited by any of the above-described exemplary embodiments, but should be defined only in accordance with the following claims and their equivalents.

What is claimed is:

1. An apparatus for conducting a capillary electrophoresis assay, the apparatus comprising:
   a cartridge housing configured to be removably installed in an electrophoresis assay device;
   a capillary array disposed in the cartridge housing, the capillary array comprising:
      an anode end and a cathode end, wherein capillaries of the capillary array at the cathode end extend out of the cartridge housing and wherein in a position of the cartridge housing installed in an electrophoresis assay device, a substantial length of the capillaries extend horizontally from the cathode end to the anode end, and
      a reservoir configured to hold an electrophoresis separation medium, the reservoir configured for use as an anode buffer reservoir during electrophoresis; and
   an injection mechanism mounted to the cartridge housing, the injection mechanism configured to deliver sample to the cathode end of the capillary array,
   wherein the housing defines a temperature control zone in which temperature is controllable in an interior of the housing at a region where the reservoir and portions of the capillaries disposed in the housing are located.

2. The apparatus of claim 1, wherein the injection mechanism is selected from a group consisting of T-injection, electro-kinetic injection, and pipette injection.

3. The apparatus of claim 1, wherein the capillaries of the capillary array have a single bend between the cathode end and the anode end.

4. The apparatus of claim 1, wherein the cartridge housing is a hard shell housing or flexible polymer housing.

5. The apparatus of claim 1, wherein the cartridge housing further comprises a top plate and a base plate.

6. The apparatus of claim 5, wherein the base plate comprises a plurality of grooves configured to receive the respective capillaries of the capillary array.

7. The apparatus of claim 1, wherein the cartridge housing is configured to be replaceably installed in the capillary electrophoresis assay device.

8. The apparatus of claim 1, wherein the cathode end is provided outside the cartridge housing, and is configured to deliver a sample to the capillary array.

9. A method for conducting biological analysis of a sample, the method comprising:
   providing a biological analysis device for conducting a biological analysis, the biological analysis device comprising a buffer source;
   installing a cartridge housing into the biological analysis device, wherein the cartridge housing holds:
      an electrode,
      an injection mechanism,
      an injection tip,
      a reservoir of a polymer, and
      a capillary array fluidically coupled to the reservoir,
      wherein the electrode has an anode end and a cathode end, wherein in a position of the cartridge installed in an electrophoresis assay device, a substantial length of the capillary array extends horizontally from the cathode end to the anode end;
   charging polymer from the reservoir into the capillary array to fill the capillary array;
   activating the electrode to pull a sample through the injection tip into an injection volume space of the cartridge housing;
   deactivating the electrode;
   inserting the injection tip into the buffer source; and
   conducting the biological analysis of the sample.

10. The method of claim 9, wherein the injection mechanism is an electro-kinetic injection mechanism.

11. The method of claims 9, wherein the injection volume space is adjacent to a sample inlet end of the capillary array.

12. The method of claim 9, wherein the electrode cathode end is adjacent to a sample inlet side of the capillary array, or the electrode anode end is adjacent to a polymer inlet side of the capillary array.

13. The method of claim 9, wherein the buffer source is an anode or cathode buffer source.

14. The method of claim 9, wherein the reservoir is a cathode or anode buffer source.

15. The method of claim 9, wherein the biological analysis device is a capillary electrophoresis device.

16. The apparatus of claim 1, wherein the cartridge is configured to be replaceable in a capillary electrophoresis assay device, the capillary array being positioned for optical access by an optical detector of the capillary electrophoresis assay device when installed in the capillary electrophoresis assay device.

* * * * *